US010052355B2

(12) United States Patent
Petyaev

(10) Patent No.: US 10,052,355 B2
(45) Date of Patent: Aug. 21, 2018

(54) PRODUCTS AND METHODS

(75) Inventor: Ivan Petyaev, Cambridge (GB)

(73) Assignee: IP Science Limited, Cambridge (GB)

(*) Notice: Subject to any disclaimer, the term of this patent is extended or adjusted under 35 U.S.C. 154(b) by 221 days.

(21) Appl. No.: 14/241,286

(22) PCT Filed: Sep. 6, 2012

(86) PCT No.: PCT/GB2012/052192
§ 371 (c)(1),
(2), (4) Date: Apr. 2, 2014

(87) PCT Pub. No.: WO2013/034911
PCT Pub. Date: Mar. 14, 2013

(65) Prior Publication Data
US 2014/0370047 A1 Dec. 18, 2014

(30) Foreign Application Priority Data
Sep. 6, 2011 (GB) .................................. 1115417.6

(51) Int. Cl.
A61K 49/00 (2006.01)
A61K 39/118 (2006.01)
A61K 39/02 (2006.01)
A61K 36/062 (2006.01)
A23L 5/00 (2016.01)
A61K 36/06 (2006.01)
C12Q 1/28 (2006.01)
C12Q 1/26 (2006.01)
A23L 31/00 (2016.01)
A23L 33/14 (2016.01)
A23L 25/10 (2016.01)
A23L 7/00 (2016.01)
A23L 33/125 (2016.01)

(52) U.S. Cl.
CPC .............. A61K 36/062 (2013.01); A23L 5/00 (2016.08); A23L 25/10 (2016.08); A23L 31/00 (2016.08); A23L 33/14 (2016.08); A61K 36/06 (2013.01); C12Q 1/26 (2013.01); C12Q 1/28 (2013.01); A23L 7/00 (2016.08); A23L 33/125 (2016.08); A23V 2002/00 (2013.01); G01N 2333/90283 (2013.01)

(58) Field of Classification Search
CPC .............................. A61K 39/00; A61K 39/002
USPC .................. 424/9.1, 9.2, 184.1, 234.1, 263.1
See application file for complete search history.

(56) References Cited

U.S. PATENT DOCUMENTS 9,375,461 B2  6/2016  Rombi

FOREIGN PATENT DOCUMENTS

| DE | 19824072 A1 | 12/1999 |
|----|----|----|
| EP | 1873235 A1 | 1/2008 |
| JP | 2003144090 | 5/2003 |
| JP | 2011148710 A | 8/2011 |
| KR | 20030018961 | 3/2003 |
| WO | WO-99/23996 A2 | 5/1999 |
| WO | 2002/063976 | 8/2002 |
| WO | WO-02/089604 A2 | 11/2002 |
| WO | WO2008/020260 * | 2/2008 |
| WO | WO-2008/020260 A2 | 2/2008 |
| WO | WO-2008/035371 A2 | 3/2008 |
| WO | 2012056024 A1 | 5/2012 |

OTHER PUBLICATIONS

Babu et al "Antioxidant and hepatoprotective effect of Acanthus ilicifolius", (2001) Fitoterapia, 72(3), pp. 272-277.
Bashmakov et al "Chalamydia trachomatis growth inhibition and restoration of LDL-receptor level in HepG2 cells treated with mevastatin", (2010) Comgarative Hepatology, 9(3) pp. 1-8.
Bashmakov et al "ApoB-containing lipoprofeins promote infectivity of chlamydial species in human hepatoma cell line", (2010) World Journal of Hepatology, 2(2) , pp. 74-80.
Benzie et al "The Ferric Reducing Ability of Plasma (FRAP) as a Measure of Antioxidant Power: The FRAP Assay", (1996) Analytical Biochemistry, 239, pp. 70-76.
Chalyk et al "Significance of determination of lipid-oxidizing catalytic antibodies in patients with ischemic heart disease" (2009) Klin Lab Diagn, 8, pp. 7-8 [English Abstract Only].
Cheng et al "Protective Effect of Monascus-Fermented Red Mold Rice against Alcoholic Liver Disease by Attenuating Oxidative Stress and Inflammatory Response", (2011) Journal of Agricultural and Food Chemistry, 59, pp. 9950-9957.
Colquhoun et al "Cheese added to a low fat diet does not affect serum lipids", (2003) Asia Pacific Journal of Clinical Nutrition 12, Supplement:S65.
Database Extract—Thomson Scientific—AN 2003-511054—XP00268667 (English language Abstract for KR 2003/0018961 A).
Database Extract from Medline: Colquhoun et al "Cheese added to a low fat diet does not affect serum lipids", Abstract No. XP002686663.

(Continued)

Primary Examiner — Rodney P Swartz
(74) Attorney, Agent, or Firm — Norton Rose Fulbright US LLP

(57) ABSTRACT

The invention relates to fungal cells and spores, as well as extracts of either, for use, in particular, in prevention or treatment of Chlamydia, or Helicobacter pylori or other infections, inflammation, inflammatory, lysosomal, acidic, SOD—or IgG or other immunoglobulin—peroxidases or hydrogen peroxide induced or other forms of oxidative damage, atherosclerosis, heart disease, stomach, intestinal and liver inflammatory conditions and their complications, promoting or stimulating regeneration or healing of wounds, burns, ulcers, or other forms of damaged or aged tissues, or in reducing elevated cholesterol and/or triglycerides levels In a preferred instance, the fungal cells or spores are those used in the manufacture of fungal fermented cheeses or other food stuff or beverages, particular fungal blue or white cheeses.

18 Claims, 6 Drawing Sheets

(56) References Cited

OTHER PUBLICATIONS

Database Abstract—Carplus—Chemical Abstracts Service—Database Accession No. 2011:755955, Lin et al—XP002686665.
Database Abstract, Carplus, Chemical Abstracts Service, Database Accession No. 2002:295614, Weibe et al—XP002686668.
Database extract WPI, Thomson Scientific AN 2003-715408, XP00268662 (English language Abstract for JP 2003/144090 A).
Frei et al "Ascorbate: The Most Effective Antioxidant In Human Blood Plasma", (1990) *Advance in Medicine Experiment and Biology*, 264, pp. 155-163.
Ghiselli et al "A Florescence-Based Method For Measuring Total Plasma Antioxidant Capability", Free Radical Biology and Medicine, vol. 18, No. 1, 1995, pp. 29-36.
Halliwell "Drug Antioxidant Effects, A Basis for Drug Selection", (1991) *Drugs*, 42, pp. 569-605.
Kimura et al "Studies on the Activities of Tannins and Related Compounds; V1. Inhibitory Effects on Lipid Peroxidation in Mitochondria and Microsomers of Liver$^2$"(1984) *Planta Medica*, 50(6), pp. 473-476.
Kuo et al (2008) *International Food Information Service (IFIS)*, FSTA Database, Database Accession No. FS-2008-09-Aj3586, XP002686666.
Lin et al "Inhibition of endothelial adhesion molecule expression by Monascus purpureus—fermented rice metabolites, monacolin K, ankaflavin, and monascin", (2011) *J Sci Food Agric*, 91, pp. 1751-1758.
Petyaev et al "Apparent superoxide dismutase-like activity of immunoglobulin", (1996) *Redox Report*, 2(6), pp. 365-372.
Petyaev et al "Superoxide Dismutase Activity of Antibodies Purified from the Human Arteries and Atherosclerotic Lesions", (1998) *Biochem Soc Trans*, 26, (S43).
Petyaev (1999) "New Catalytic Properties of Superoxide Dismutase Biological and Medical Implications", *Superoxide Dismutase: Recent Advances and Clinical Applications*, Paris, pp. 40-44.
Petyaev et al "Superoxide Dismutase Activity of Antibodies Purified From Human Atherosclerotic Lesions", (1999) *Superoxide Dismutase: Recent Advances and Clinical Applications*, Paris, pp. 51-54.
Petyaev et al "Monoclonal Antibodies Against Lipopolysaccharide of Chlamydia trachomatis with Cross Reactivity to Human ApoB", (2011) *Hybridoma* 30(2), pp. 131-136.
Petyaev (2005) "Lipid Oxidising Chlamydia Antibodies as a New Drug Target in the Treatment of Atherosclerosis", *12th World Congress on Heart Disease—New Trends in Research and Treatment, Vancouver Canada*, pp. 1-6.
Petyaev et al "Isolation of Chlamydia Pneumoniae From Serum Samples of the Patients with Acute Coronary Syndrome", (2010) *International Journal of Medical Sciences*, 7(4), pp. 181-190.
Rice-Evans et al "Antioxidant Status In Plasma And Body Fluids", (1994) *Methods in Enzymology* 234, pp. 279-293.
Sanbongi et al "Antioxidative Polyphenols Isolated from Theobroma cacao", (1998) *Journal of Agricultural and Food Chemistry*, 46 (2), pp. 454-457.
Vani et al "Antioxidant Properties of the Ayurvedic Formulation Triphala and its Constituents", (1997) *International Journal of Pharmacognosy*, 35(5), pp. 313-317.
Wiebe "Myco-protein from Fusarium veneatum: a well-established product form human consumption", (2002) *Applied Microbiology and Biotechnology*, 58(4), pp. 421-427.
Rizzello, C.G., et al; Antibacterial Acivitied of Peptides form the Water-Soluble Extracts of Italian Cheese Varieties; J. Dairy Sci. 88:2348-2360; American Diary Science Association, 2005.
Wu et al., "Preliminary Study on Antioxidant Substances in the Penicillium Culture Medium", Food and Fermentation Industries, vol. 3, p. 55-59, Mar. 2010, published on Mar. 31, 2010.
Japan Society for Bioscience, Biotechnology, and Agrochemistry, Proceedings of Annual Meeting 2007 "Search for microorganisms producing antifungal substances from fermented foods", p. 178 (3A09p13).
Japan Society for Bioscience, Biotechnology, and Agrochemistry, Proceedings of Annual Meeting 2008 " Isolation of antifungal substance producing bacteria from cheese derived microbial community", p. 261 (3A25p01).
Japan Society of Nutrition and Japan Society of Nutrition and Food Science, Proceedings of Annual Meeting, 2010, "Suppression of dextran sulfate (DSS)-induced mouse colitis by natural cheese intake", vol. 64, p. 179 (3B-05p).
Clèment et al. "Purification and Identification of Bovine Cheese Whey Fatty Acides Exhibiting In Vitro Antifungal Activity", J. Dairy Sci., 2008, vol. 91, No. 7, pp. 2535-2544.
Panagiotakos et al., "Dairy Products Consumption is Associated with Decreased Levels of Inflammatory Markers Related to Cardiovascular Disease in Apparently Healthy Adults: The ATTICA Study", J. Amer. College of Nutr., 2010, vol. 29, No. 4, pp. 357-364.
3A09p13 Search for microorganisms producing antifungal substances from fermented foods (Machine translation provided).
3A25p01 Isolation of antifungal substance producing bacteria from cheese derived microbial community (Machine translation provided).
3B-05p Suppression of dextran sulfate (DSS)-induced mouse colitis by natural cheese intake (Machine translation provided).
Sprong et al., "Dietary cheese whey protein protects rates against mild dextran sulfate sodium induced colitis: Role of mucin and microbiota", J. Diary Sci., 2010, vol. 93, No. 4, pp. 1364-1371.

* cited by examiner

PRODUCTS AND METHODS

CROSS REFERENCE TO RELATED APPLICATIONS

This application is a national phase application under 35 U.S.C. § 371 that claims priority to PCT Application No. PCT/GB2012/052192 filed on Sep. 6, 2012, which claims the benefit of Great Britain Application No. 1115417.6 filed Sep. 6, 2011, all of which applications are incorporated herein by reference in their entireties.

TECHNICAL FIELD OF THE INVENTION

The present invention relates to nutritional, cosmetic, preventive and therapeutic applications of food fungi, fermentation products and extracts thereof. The invention relates in particular to lowering elevated cholesterol and/or triglycerides levels, as well as to treating or preventing infection, inflammation, inflammatory damage, atherosclerosis, heart disease, stomach, intestinal and liver inflammatory conditions and their complications, and to promoting or stimulating regeneration or healing of wounds, burns, ulcers, or other forms of damaged or aged tissues.

BACKGROUND OF THE INVENTION

Chronic inflammatory processes in the liver and adipose tissues result in lipid abnormalities and Metabolic Syndromes. Chronic inflammation in other tissues also has a number of clinical implications including atherosclerosis, cardio-vascular disease, obesity, diabetes type 2, cancer, sarcopenia, gastritis, stomach or duodenum ulcers, arthritis, dermatological diseases and aging of skin and other organs. There are a number of reports associating the development of those conditions with the presence of *Chlamydia* infection. Mechanisms for how *Chlamydia* infection can reach the liver, alter lipid metabolism and trigger oxidative cascades have recently been reported [5-10].

Cytokines and in particular interleukins, lymphokines, and interferons are important in controlling inflammatory reactions and the infection process.

inflammatory oxidative damage can result from bacterial infection, or autoantibodies, or the presence of other toxic factors, or when inflammation reaches a critical level. Damage to the cell membrane can result in the release of cell contents into the extracellular environment. The cell contents can include proteases, other degradation enzymes and acidic intracellular components. The release of the cellular contents into the extracellular environment can result in further damage to cell membranes and the intracellular matrix. Moreover, the acidic shift in local pH can alter the peroxidase activity of superoxide dismutases and other proteins with similar structural and catalytic properties [3-4].

Conditions involving inflammation and inflammatory damage are of ever increasing importance. Levels of heart disease and diabetes are steadily increasing, driven, in part by high levels of obesity.

SUMMARY OF INVENTION

The inventors have discovered that food fungi and their fermentation products have a range of previously uncharacterized and beneficial biological properties, including anti-infective, anti-inflammatory, and anti-oxidative properties, as well as being able to stimulate tissue regeneration. The effect is seen in particular with fungi used in the production of blue and white fungal fermented cheese or other foodstuffs using such fungi.

Compositions described herein may, for example, reduce or inhibit infection, inflammation or oxidation, including inflammatory oxidative damage, in the individual or reduce or inhibit the onset, duration or severity of one or more symptoms associated with infection, inflammation or oxidation in the individual or reduce the risk of the individual suffering from infection, inflammation or oxidation or one or more symptoms associated therewith. The compositions may be used to lower cholesterol and hence help reduce the incidence, or delay the onset of, heart disease, as well as helping promote recovery in heart disease, particularly after a heart attack. The invention may be used in particular to lower elevated cholesterol levels and/or triglyceride levels in an individual.

In one preferred instance, the invention may be used to lower or reduce cholesterol and/or triglycerides and in particular to lower elevated cholesterol and/or triglycerides levels, including in subjects known to have atherosclerosis and/or heart disease, but also healthy subjects. Given cheese is perceived as a high fat food, such a finding is unexpected. The compositions and methods of the invention may also be used to prevent, reduce or treat infection.

Hence, the invention provides for use in prevention or treatment of infection, inflammation, inflammatory damage, oxidative damage, atherosclerosis, heart disease, a stomach, intestinal or liver inflammatory condition or complication thereof, promoting or stimulating regeneration or healing or in reducing elevated cholesterol and/or triglycerides levels.

Accordingly, the present invention provides a composition comprising:
(i) a population of cells and/or spores of a food fungus;
(ii) a food matrix comprising a population of cells and/or spores of a food fungus; and/or
(iii) an extract, fermentation product or metabolite of (i) or (ii), for use in the prevention or treatment of infection, inflammation, inflammatory damage, oxidative damage, atherosclerosis, heart disease, a stomach, intestinal or liver inflammatory condition or complication thereof, promoting or stimulating regeneration or healing or in reducing elevated cholesterol and/or triglycerides levels.

The invention further provides for use of a composition comprising: (i) a population of cells and/or spores of a food fungus; (ii) a food matrix comprising a population of cells and/or spores of a food fungus; and/or (iii) an extract, fermentation product or metabolite of (i) or (ii), in the manufacture of a medicament for prevention or treatment of infection, inflammation, inflammatory damage, oxidative damage, atherosclerosis, heart disease, a stomach, intestinal or liver inflammatory condition or complication thereof, promoting or stimulating regeneration or healing or in reducing elevated cholesterol and/or triglycerides levels.

The invention additionally provides a method for prevention or treatment of infection, inflammation, inflammatory damage, oxidative damage, atherosclerosis, heart disease, a stomach, intestinal or liver inflammatory condition or complication thereof, promoting or stimulating regeneration or healing or in reducing elevated cholesterol and/or triglycerides levels, the method comprising administering to an individual in need thereof a composition comprising: (i) a population of cells and/or spores of a food fungus; (ii) a food matrix comprising a population of cells and/or spores of a food fungus; and/or (iii) an extract, fermentation product or metabolite of (i) or (ii).

The invention further provides a fungal cheese, an extract from such a cheese, or a food or beverage or supplement comprising either such a cheese or extract, for use in prevention or treatment of infection, inflammation, inflammatory damage, oxidative damage, atherosclerosis, heart disease, a stomach, intestinal or liver inflammatory condition or complication thereof, promoting or stimulating regeneration or healing or in reducing elevated cholesterol and/or triglycerides levels.

In a further embodiment, the invention provides a method for producing an extract for use in prevention or treatment of infection, inflammation, inflammatory damage, oxidative damage, atherosclerosis, heart disease, a stomach, intestinal or liver inflammatory condition or complication thereof, promoting or stimulating regeneration or healing or in reducing elevated cholesterol and/or triglycerides levels in an individual, comprising: (a) providing a food matrix comprising a population of cells and/or spores of a food fungus; (b) admixing said food matrix in a liquid phase and; (c) isolating the liquid phase to produce the extract.

The invention also provides a method to screen, identify or assess activity of a molecule, compound or product that can inhibit inflammatory damage, lysosomal damage, acidic damage, SOD- or IgG or other immunoglobulin medicated damage, peroxidase or hydrogen peroxide induced damage, or other forms of oxidative damage, the method comprising: (a) providing a protein or proteins with a Greek key domain, which capable of forming an electron-transfer complexes in a proton excess over electron production, in an acidic environment with pH between 4.0-4.5 and below 6.0-6.5; and (b) monitoring for the generation of hydrogen peroxide and/or the oxidation due to the generation of hydrogen peroxide.

The invention additionally provides an assay for assessing inflammatory oxidative damage (IOD) comprising: (a) providing a human tissue sample, tissue sample homogenate, serum or plasma; (b) adding a source of hydrogen ions capable of acting as a substrate for super oxide dismutase; (c) incubating the sample for from 6 to 24 hours; and (d) performing an MDA test to determine the level of oxidation.

DETAILED DESCRIPTION

Figure 1:
FIG. 1 shows examples of Roquefort cheese used as one source for active extracts (top) and Ossau-Iraty as the control non-fungal cheese (bottom).

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature. Where the term "about" is used the application also discloses employing the exact value specified. The present invention is based on the finding that fungal cells and spores from fungi used in food production, particular cheese production, have a number of unexpected properties which mean they are useful in a range of applications, such as treating or preventing infection, reducing inflammation and inflammatory damage and reducing cholesterol levels.

Fungi and Compositions

Any suitable fungus may be employed in the invention. The food fungus may be, for instance, selected from a fungus or mould of the *Penicillium* genus, such as *Penicillium roqueforti, Penicillium camemberti, Penicillium candidum, Penicillium glaucum* or *Penicillium nalgiovense*; a fungus or mould of the *Rhizopus* genus, such as *Rhizopus oligosporous*; a fungus or mould of the *Fusarium* genus, such as *Fusarium venenatum*; a fungus or mould of the *Monascus* genus, such as *Monascus pilosus*, or *Monascus purpureus*, or *Monascus ruber*; or a fungus or mould of the *Aspergillus* genus, such as *Aspergillus oryzae* or *Aspergillus terreus*.

Any food fungus used in cheese production may be employed in the invention, particularly those used in making blue or white fungal cheeses, including any of the fungi used to make the cheeses discussed herein. The fungus may be one used in the production of a soft cheese, particularly a soft blue or white fungal cheese. Fungal cells, fungal spores or extracts of either may be employed in the invention. Preferred food fungi include *Penicillium roqueforti* and *Penicillium camemberti*. In some preferred embodiments, the food fungus does not produce penicillin, and is not *Penicillin notatum* or *Penicillium chrysogenum*.

The fungal cells, spores, extracts and metabolites of such fungi may be employed in various compositions due to the unexpected properties outlined herein. In one instance, the fungal cells, spores, extracts, metabolites and compositions of the invention are provided for use in a method of treatment of the human or animal body.

A composition of the invention may be a food product, food additive, dietary supplement, topical or nutra-cosmetic, nutraceutical product pharmaceutical product or other composition suitable for ingestion by the individual. The composition may be, for instance, in tablet form or be provided as a liquid. In one preferred instance, the invention provides a supplement comprising the fungal cells or spores of the invention, or an extract thereof. The supplement may be in the form of a drink.

Suitable food products include dairy products, such as cheese; meats, such as cured meats; other foods, beverages and animal, marine, plant, yeast, or microbial biomass. In one instance, the composition is in the form of a yoghurt or a health drink. The composition may be a milkshake or other health drink. The composition may be an ice cream. The composition may be a sauce or mayonnaise. Other suitable food products will be apparent to those skilled in the art. In some instances, the fungal cells, spores or extract thereof will be added to, or coated on, a food product, for instance onto bread.

In some preferred embodiments, the food product or food matrix is cheese. In one preferred instance, the cheese is a blue or soft cheese, particularly such a cheese which has had added a fungus as part of its preparation, or added to it at some stage in preparation, including any of those referred to herein. Hence, in a preferred instance the cheese is a fungal cheese. In a preferred instance, the cheese is a blue or white fungal cheese. The cheese may be a veined cheese. Suitable cheeses include Roquefort; Camembert; Danish Blue cheese; Creamy Blue; Stilton; Cabrales, Blue Brie, Cambozola; Fourme d'Ambert; Gorgonzola; Bleu d'Auvergne and Cibosano and other mould containing cheeses. The cheese may be a cheese which is not usually made with a fungus, but to which a fungus of the invention has been added to augment the cheese. The cheese may be, in some instances a French cheese and in others a Danish cheese.

The cheese may be, for instance, a cheese made from, or comprising, cow, sheep, goat or buffalo milk. The cheese may be pasteurised or unpasteurised. The cheese may have been subjected to UHT treatment. Any of the compositions discussed herein may have been pasteurised or UHT treated or may be unpasteurised. In some instances, the fungal cells or spores in the cheese, or other compositions of the invention, may be live, in others treatment may have killed the fungal cells and/or spores. In one preferred instance, the food or other product of the invention, comprises a fungus used in cheese making, or an extract from such a fungus.

Extracts and Measurement of Activity

An extract of a food matrix or a food fungal population may be employed or provided and comprise one or more molecules or compounds produced by the food fungus, including proteins, glycoproteins, lipoproteins, polysaccharides, and secondary metabolites. The molecules or compounds may be produced by the metabolism of the food matrix by the food fungus. The extract may, in some cases, be an extract from a whole cheese or from a culture of a fungus used in cheese preparation.

A suitable extract of a food matrix or fungal population may be produced by mixing the matrix or population with a liquid phase and isolating the liquid phase. For example, a method for producing an extract for use as described herein may comprise: (a) providing a food matrix comprising a population of cells or spores of a food fungus; (b) admixing the food matrix with a liquid phase; and (c) isolating the liquid phase to produce the extract.

Suitable liquid phases include aqueous buffers, such as phosphate buffered saline (PBS); organic solvents such as methanol and ethanol; acids as hydrochloric acid; and acid/alcohol mixtures such as ethanol and hydrochloric acid. Other suitable aqueous buffers, organic solvents, acids and combinations thereof would be apparent to the persons skilled in the art. Any liquid phase which results in an extract showing one or more of the activities of the invention may be employed in the invention. For example, the extract or metabolite may show anti-microbial, anti-inflammatory, and/or anti-oxidative activity. The extract or metabolite may display the ability to stimulate or enhance regenerate, including tissue regeneration, such as regeneration of any of the types of tissue damage mentioned herein.

In some embodiments, the food matrix or fungal population and the liquid phase may be homogenized, for example by vortexing, sonication or other convenient mixing technique. The liquid phase may be separated or isolated from the admixture by any convenient technique, such as centrifugation, gel or membrane filtration, or any other convenient separation technique. In one instance a supernatant following resulting from centrifugation may be employed.

In some instances, the extract may be obtained from a cheese or from a stage in the production of a cheese. In some cases, rather than prepare a cheese, the fungus is simply fermented and an extract obtained from the culture, preferably the fungus will be one used in the preparation of cheese.

The extract may be pasteurised or sterilised, e.g. by filtration, or by any other convenient sterilisation technique.

In some embodiments, the extract may be further fractionated, for example by electrophoresis, or gel or membrane filtration, HPLC or other convenient technique to produce a fraction which is enriched for one or more proteins, including glycoproteins or lipoproteins, polypeptides, (lipo-)polysaccharides or other organic molecules or components of the extract. Filtration using sephadex may be employed.

One or more fractions of the extract may be subjected to further analysis, for example by HPLC or mass-spectroscopy.

Any extract or fraction may be employed in the invention that retains the desired activity, for instance the desired anti-microbial, anti-inflammatory or anti-oxidative activity. The extract or fraction may display the ability to stimulate or enhance regeneration/The anti-oxidative, anti-inflammatory, anti-infective or regenerative activity of one or more fractions of the extract may be determined following fractionation. In one case, the extract or fraction may be one which displays anti-microbial activity, such as antibacterial or anti-fungal activity and in a preferred instance against *Chlamydia*. The fraction or extract may display anti-oxidative activity in an assay of the invention, particularly in any of the assays described below for assessing inflammatory oxidative damage.

In another instance, the fungal cells/spores, extract thereof, metabolite or fermentation product will be one capable of lowering cholesterol levels, particularly LDL cholesterol, and/or may be capable of lowering triglyceride levels. It may be capable of lowering those levels where elevated in comparison to what would be expected for a healthy subject.

A composition comprising (i) a population of cells of a food fungus, (ii) a food matrix comprising a population of cells of a food fungus or (iii) an extract, fermentation product or metabolite of (i) or (ii), may reduce or inhibit one or more parameters associated with inflammation, infection or oxidation in the individual. For example, the composition may reduce or inhibit one or more of allergic processes; endothelial damage; inflammation, for example in the development of organ diseases; oxidative damage; inflammatory oxidative damage; lipid peroxidation, the concentration of the enzymes AST and ALT in the liver; serum cholesterol levels or cholesterol LDL particle levels; liver lipids and triglycerides; inflammation; LPS-mediated cell recruitment to the peritoneal cavity and production and recruitment of pro-inflammatory cytokines in the individual.

A composition or extract as described herein may reduce or inhibit the activity of one or more of serum glutamate pyruvate transaminase, serum glutamate oxaloacetate transaminase, alkaline phosphatase and other lysomal enzymes, metalloproteases, collagenases, glucuronidase, and other enzymes and factors which affect one or more of cellular coating, extra-cellular matrix, cross-linked collagen, sialic acid and other markers of damage to the cell coating and matrix. In a preferred instances, the enzyme or marker modulated will be one associated with a disease or condition, particularly one of those referred to herein.

Subjects and Administration

The invention may be used to treat any suitable subject, for example any suitable mammalian subject. In one preferred instance, the subject is human. The invention may also be used to treat animals, such as farm animals and pets, for example horses, cattle, sheep, dogs and cats.

The individual may have a condition selected from the group consisting of infection, auto-immune disease; allergic conditions; hypertension; atherosclerosis; cardio pathologies, such as Coronary Heart Disease; vascular pathologies, such as endocarditis, myocarditis, heart failure, heart valve disease, arrhythmias, atherosclerosis, hypertension, vasculitis, endarteritis, varicose veins, endophlebitis, endothelial damage; cerebral pathologies; obesity; diabetes type 2; cancer, sarcopenia; metabolic dysfunction; Metabolic Syndrome; cellulite and aging tissue degradation; gastritis; stomach or duodenum ulcers; or arthritis; or dermatitis, psoriasis, acne, chronic skin ulcerations, or other age-related or not skin conditions, including skin and other tissues burns and wounds; sport, trauma, operation and other injuries; cachexia, side-effects of chemotherapies and radiation treatment, or radiation exposure; may be at risk of such a condition.

In one preferred instance, the subject to be treated may have elevated cholesterol and/or triglycerides levels.

In one instance, the subject may be one with heart disease and/or atherosclerosis or be a subject in a group identified to be at risk from such conditions. The subject may have raised cholesterol and/or may be taking statins. The subject may be taking aspirin to help prevent heart disease. The subject may have had at least one heart attack. The subject may be one who has had a stroke. The subject may be a healthy subject, but may be administered a composition of the invention to help reduce the rate of, the severity, or onset of atherosclerosis and/or heart disease.

In a further preferred instance, the invention may be used to treat or prevent infection.

The subject may therefore be one with an infection, such as an infection with any of the microbes referred to herein and in particular *Chlamydia*. In one instance, the subject may be one with elevated, or high cholesterol. The subject may have both elevated cholesterol and test positive for *Chlamydia*. The subject may be one who is overweight or obese. The subject may be, for instance, over 30, 40, 45, 50, 60, 67 or 70 years in age.

The invention may also be used to treat or prevent *Helicobacter pylori* infection. The invention may be used to treat or prevent ulcers associated with *Helicobacter pylori* infection. The subject to be treated using the invention may be one with an ulcer and/or a history of ulcers.

The invention may also be used to stimulate or enhance tissue regeneration. For example, the invention may be used to treat a wound, a burn, a ulcer or other tissue damage. The invention may be used to treat or prevent inflammatory damage and/or oxidative damage. The invention may be used to treat lysosomal, acidic, SOD, peroxidise, immunoglobulin or other forms of damage.

The invention may also be used to treat stomach, intestinal or liver conditions, particularly such conditions resulting from inflammatory damage. In one instance, the condition is an ulcer.

Compositions as described herein may be useful in the treatment of the condition discussed herein or the alleviation of one or more symptoms. For instance, the invention may result in a reduction in cholesterol, a reduction or elimination of infection, a reduction in inflammatory oxidative damage. In one instance, treatment using the invention may result in elevated cholesterol and/or triglyceride levels being reduced and in particular to a level which would be classified as normal for the subject. Any of the compositions described herein may be used to reduce the risk of, or rate of, heart disease, atherosclerosis and/or heart attacks, as well as strokes. In one instance, any of the cheeses or foodstuffs described herein may be used for such a purpose, particularly such conditions linked to *Chlamydia* infections, or where the subject has such an infection.

The subject may be one with an infection. Infection may include infection with bacteria, for example gram positive bacteria, including Staphylococci such as *Staphylococcus saprophyticus*, and gram negative bacteria, including *E. coli*, such as *E. coli* 0157, *Chlamydia*, such as *Chlamydia trachomatis*, and *Chlamydia pneumoniae*; infection with a fungus, for example *Candida*, such as *Candida albicans*, infection with protozoa; infection with *rickettsia*; or infection with a virus. The invention may be used against *S aureus*. The subject may have pneumonia or septicaemia, for instance such a condition caused by infection and in particular due to a *Chlamydia* infection. The subject may have a *Helicobacter* infection and in particular a *Helicobacter pylori* infection. The subject may also have an ulcer or a history of ulcers.

The subject may have an infection and tissue damage, such as a burn, wound or other form of tissue damage.

A composition comprising (i) a population of cells of a food fungus, (ii) a food matrix comprising a population of cells of a food fungus or (iii) an extract, fermentation product or metabolite of (i) or (ii), as described above, may be administered in any convenient form or formulation. For example, such compositions and formulations may be administered as cosmetic, nutraceutical or pharmaceutical compositions comprising together with one or more pharmaceutically, cosmetically or nutritionally acceptable carriers, adjuvants, excipients, diluents, fillers, buffers, stabilisers, emulsifiers, preservatives, lubricants, or other materials well known to those skilled in the art and, optionally, other active agents. Suitable materials may be generally recognized as safe (GRAS) in accordance with the US FDA criteria and may include staple foodstuffs as described below. The composition may be added to the diet of the subject.

In some instances, compositions of the invention may be packaged with labelling or instructions highlighting the uses and benefits of the invention. For instance, the invention includes any of the compositions discussed herein with an indication of any of the activities outlined herein such as an indication of the anti-infective, anti-inflammatory and/or cholesterol lowering properties of the composition, particularly the cholesterol lowering properties of the composition. In one instance, the invention provides a food product, such as a cheese or cheese based product, packaged in that way, for instance for any of those cheeses mentioned herein, particularly the blue cheeses mentioned herein, including Roquefort. Such packaging may also be present for any of the fungal cheeses referred to herein, including the white fungal cheeses, as well as the blue fungal cheeses.

In some embodiments, compositions described herein may be formulated for topical administration to an individual. Suitable formulations and topical administration methods are well known in the art. In some instances, a composition of the invention may be administered to the site of tissue damage, for instance to a wound or burn. The composition may be, for example, applied via a bandage, poultice, implant, or other means of localising delivery to the site of damage. The composition may be in the form of a gel, an ointment or be administered as a spray.

In a preferred embodiment, the compositions and methods of the invention involve oral administration or consumption. In some instances, the compositions of the invention are eaten as part of the diet.

Compounds, materials, compositions, and/or dosage forms may be used which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The invention may take the form of a supplement or health food. In one instance, a tablet, yoghurt, or drink comprising the fungal cells or spores, or an extract or metabolite thereof may be provided. A food which does not normally comprise fungal cells or spores, or at least fungal cells or spores used in a cheese, may be supplemented with such cells or spores or an extract from either.

In some cases, the composition of the invention may be one which would usually contain the fungal cells, spores, extract or metabolite of the invention, but has been augmented with a higher amount. For instance, a foodstuff of the invention, such a cheese, may have a higher level of the fungal cells, spores, extract or metabolite, in one preferred instance the foodstuff is, or comprises, such an augmented cheese. For example, the cheese may have at least 10%, 20%, 50%, 100%, 200%, 300% or more of the fungal cells, spores, extract or metabolite of the invention. The packaging for the product may indicated that it is an augmented or improved product due to the presence of the elevated level of fungal cells, spores, extract or metabolites.

Assays

Other aspects of the invention relate to the identification and characterization of food products with anti-infection, anti-inflammatory and/or anti-oxidative properties, as well as those with regenerative abilities. For example, a method of identifying or characterizing a food product may comprise: providing a food product which comprises a population of cells or spores of a food fungus and; measuring the activity of a sample or extract of food product in reducing infection, inflammation or oxidation. The ability to promote tissue regeneration may be measured.

The method may comprise the initial step of selecting or identifying a food product which comprises a population of cells of a food fungus. Suitable food fungi are described above.

The ability of the extract or sample to reduce or inhibit allergic processes; endothelial damage; inflammation, for example in the development of organ diseases; oxidative damage; inflammatory oxidative damage; inflammation; or recruitment of pro-inflammatory cytokines in an in vitro or in vivo model system may be determined.

The ability of the extract or sample to reduce or inhibit the activity of one or more of serum glutamate pyruvate transaminase, serum glutamate oxaloacetate transaminase, alkaline phosphatase and other lysomal enzymes, metalloproteases, collagenases, glucuronidase, and other enzymes and factors which affect one or more of cellular coating, extra-cellular matrix, cross-linked collagen, sialic acid and/or other markers of damage to the cell coating and matrix may be determined.

The activity of the sample or extract in reducing infection may be determined. For example, the effect of the sample or extract on one or more pathogen cells, such as bacterial, or fungal, or protozoa cells, or *rickettsia*, or viral particles may be determined. A method comprise contacting the sample or extract with pathogen cells and determining the effect of the sample or extract on the number, growth, viability or infectivity of the pathogen cells. A decrease in the number, growth, viability or infectivity of pathogen cells contacted with the sample or extract, relative to controls is indicative that the food product has anti-infective properties. Other suitable in-vitro, or ex-vivo, or in-vivo tests for anti-infective properties are well known in the art. Hence, in one instance, the compositions and other substances of the invention will show anti-infective activity, particularly in such assays, especially again *Chlamydia*.

The activity of the sample or extract in reducing inflammation may be determined. For example, the effect of the sample or extract on the expression or production of cytokines in a mammalian cell may be determined. A method comprise contacting the sample or extract with mammalian cells and determining the effect of the sample or extract on the expression, production or secretion of cytokines by the mammalian cells. A decrease in the expression, production or secretion of cytokines following contact with the sample or extract, relative to control cells not contacted with the sample or extract, is indicative that the food product has anti-inflammatory properties.

In other embodiments, the production of nitric oxide (NO) and PGE2 by lipopolysaccharide (LPS)-stimulated mammalian cells, such as RAW 264.7 cells, may be determined.

The activity of the sample or extract in reducing inflammation may be determined in an acute inflammation rodent model, such as induced paw oedema models, for example a carrageenan-induced paw oedema model, or a chronic inflammation rodent model, such as cotton pellet granuloma and induced air-pouch models. Other suitable in-vitro, or ex-vivo, or in-vivo tests for anti-inflammatory properties are well known in the art (see for example, Rubinchik et al Methods Mol. Biol. 2010; 618:349-58).

The method may measure the concentration of cytokines. Suitable cytokines are well known in the art and include IL-1B, IL-2, IL-4, IL-6, IL-8, IL-10, BM-CSF (bovine macrophage colony-stimulating factor), IFN-γ, TNF-α, or other cytokines or signalling molecules. Methods for measuring cytokines are well known in the art. Compositions of the invention may, in some instance, reduce cytokine levels, for instance may reduce any of the above mentioned cytokines except BM-CSF or INFN-γ.

In other embodiments, the effect of the sample or extract on LPS-mediated cell recruitment in a mammal model may be determined. For example, dose-dependent titration of extract solutions in a test-system compared to a solvent only control may be performed.

The activity of the sample or extract in reducing oxidation and/or inflammatory oxidative damage may be determined. For example, dose-dependent titration of extract solutions in a test-system compared to a solvent only control may be performed.

Suitable methods for measuring anti-oxidative properties include conjugated diene assays (Beris, H. Drugs, 42, 1991, 569-605); DPPH assays (Vani et al Inter. J. Pharmacognosy 35, 1997, 313-317); superoxide or hydroxyl radical scavenging activity (Babu et al Fitoterapia, 72, 2001, 272-277); ABTS assays; DMPD assays (Rice-Evans, C et al Methods Enzymol, 243, 1994, 279-293); Oxygen Radical Absorbance Capacity (ORAC) (Frei et al *Advances in medicine experiment and biology,* 264, 1990, 155-63); FRAP (Benzie et al Anal. Biochem., 239, 1996, 70-76); TRAP (Ghiselli et al Free Radic. Biol. Med., 18, 1995, 29-36); erythrocyte ghost assays (Chiaki et al *J. Agric Food Chem:* 46: 454-57) and microsomal lipid peroxidation or thiobarbituric acid (TBA) assays (Kimura, Y et al (1984) *Planta Med:* 50: 473-76). Other suitable in-vitro, or ex-vivo, or in-vivo tests for anti-oxidative properties are well known in the art The methods described above may be conducted in vitro, for example in cell culture. The methods described above may be conducted in vivo, for example utilizing a host or model organism. The methods may use ex vivo samples.

A score or grade may be assigned to the food product based on the measured activity in 1, 2, 3 or more tests as described above. For example, a score or grade on an incremental scale of up 2, 3, 4 or 5 more scores or grades may be assigned or allocated to the food product, depending on the amount of anti-infection, anti-inflammation or anti-oxidation activity measured for that product. A score or grade may be represented by a number (e.g. 1, 2 or 3), a descriptive grade (e.g. high, medium or low activity) or a combination (e.g. one star, two star or three star activity). A score may also be given for regenerative ability.

In some embodiments, the score or grade may be defined relative to a reference food product, such as Roquefort cheese. For example, a three increment scale may comprise a first increment which is assigned to measured activities lower than the reference product, a second increment which is assigned to measured activities similar to the reference product and a third increment which is assigned to measured activities greater than the reference product. The provision of other suitable scales is well within the ability of the skilled person.

In some embodiments, the score or grade may be displayed on the packaging of the food product. For example, the food product or packaging may be labelled with the assigned score or grade. Typically, the packaging or surface of the food product may comprise a marking or other identifier which indicates the assigned score or grade. Suitable methods of labelling food products and packaging are well known in the art.

The methods described above may be used to compare different food products, or extracts of food products. For example, the score or grade may be assigned to a food product according to the relative ability of the food product to inhibit inflammation; inhibit anti-oxidative damage; or inhibit pathogen infection, compared to other food products.

In some instances, administration of a composition of the invention may result in reduction of cholesterol and/or triglyceride levels. For instance, in some cases, the invention may result in a reduction of cholesterol to below 300 mg/dL, in particular below 250 mg/dL and preferably to 200 mg/dL or lower. It may result in a reduction in liver enzymes, such as ALT and AST.

In a further instance, a composition of the invention may show the ability to reduce or prevent infection with any of the infectious agents mentioned herein, including those employed in the Examples of the present application. The composition may show activity against *Chlamydia* and in particular against *Chlamydia trachomatis*. Such activity may be tested for in vitro, for instance via adding the composition to a set amount of *Chlamydia* in culture. Activity may be tested in animal models, for instance in mice infected with *Chlamydia*, such as *Chlamydia muridarum*, including the MoPn strain. The assay may look for increased survival time in comparison to infected mice not administered the composition.

In one preferred instance, a composition of the invention may display a reduction in IOD (inflammatory oxidative damage), for instance as measured using an assay described herein.

The invention also provides an assay comprising providing a tissue sample or a homogenate of tissue sample, or serum/plasma, preferably from patients with chronic inflammatory or oxidative stress conditions, acidifying the sample, using a substrate or substrates for superoxide dismutatse (SOD), incubating the sample, then performing a malondialdehyde (MDA) test, or other suitable assays to measure products of peroxidation. In a preferred instance, the results where a composition of the invention has been added are compared to a control sample.

The tissue may be any human tissue, for instance tissue recovered from an operation, similarly homogenates of any such tissue may be employed in the assay. In a preferred instance, the tissue or tissue homogenate is human in origin. In a further preferred instance, the assay is performed using plasma or serum. In some instances, the sample used is selected from blood plasma, blood serum, a blood plasma or serum fraction, an arterial wall sample, a liver tissue sample, a skeletal muscle sample, adipose tissue, a skin tissue sample, a stomach or intestinal wall sample, or a homogenates of any such sample.

In one instance, the tissue, homogenate, serum, or plasma is from an individual with a chronic inflammatory or oxidative stress condition, including any such conditions referred to herein, for instance atherosclerosis or arthritis. Such tissues, homogenates, serum or plasma may be, for instance, from a subject with an inflammatory bowel disorder, coronary heart disease, hypertension, hypercholesterolemia or SLE.

In some instances of the assay, the initial sample is adjusted so that the level of protein in the sample is from 1 to 10 mg protein per ml of sample, for example from 2 to 8 mg/ml, preferably from 3 to 7 mg/ml, for instance from 4 to 6 mg/ml or about such values. In some instances, the level of protein is about 5 or 6 mg/ml. In a further preferred instance, the addition of the test sample will not dilute the overall sample volume by more than about 20%, 15%, 10% or 5% and preferably will keep the level of protein in the overall sample within the above specified ranges.

In a further preferred instance, acetic acid or hydrochloric acid is provided as a source for hydrogen ions to act as a substrate for SOD. In some cases, the concentration of hydrogen ions is at least about 10, 25, 50, 75, 100, 125, 150, 175 or 200 fold higher than the level of such ions in the control sample, or up to such levels. For instance, in some cases the level of hydrogen ions added may be from about 50 to 150, preferably from 75 to 125 and in particular 100 fold greater than in the control sample. In one instance, an equivalent volume of liquid is added to the control sample, but without the source of hydrogen ions, for instance PBS may be added to ensure the volume of the control is equivalent to that of the test sample.

Following addition of the source of hydrogen ions, the sample may be, for example, incubated for from about 6 to 24 hours, such as from 6 to 16, or 8 to 12 hours. In one preferred instance, the samples are incubated overnight. The incubation may be, for instance, at 37° C. Following incubation, the reaction may be stopped using, for instance, trichloric acid, for example by adding about 0.5 to 1M trichloric acid.

An MDA test may then be performed to analyse the level of oxidation. The sample to which the test sample has been added may be compared to a negative control to which the source of hydrogen ions has not been added. For example, two equivalent reactions, except for the addition of hydrogen ions may have been performed. In some cases, a positive control may also be performed, such as one including a test sample known to alter inflammatory oxidative damage (IOD), such as one known to inhibit IOD. In one instance, the amount of MDA is quantified using the ability of MDA to react with thiobarbituric acid (TBA), followed by quantification, such as spectrophotometric or fluometric quantification.

In one instance, fungal cells or spores, fungal extracts or other compositions employed in, or provided by, the invention will inhibit IOD, such as IOD as measured in the above described assay. For instance, the level of inhibition in comparison to the control may be at least 10, 20, 30, 50 or 40% or up to such levels. In some instances, the level of inhibition may be at least 10, 15, 25, 30, 40, 50, 60, 75, or 100% of that shown by Roquefort cheese, such as any of the types of Roquefort cheese or extracts thereof referred to therein. The level of inhibition may be at least such levels in comparison to that shown by Castello or Camembert cheese, such as any specific form of those cheeses or extracts thereof referred to herein. In some instances, Ossay-Iraty or other non-fungal cheeses may be used as a negative control which display no, or minimal inhibition of IOD. In one instance, the assay used to determine the level of inhibition of Inflammatory Oxidative Damage will use human serum as the sample and in particular will be the same assay as used to produce the results described in Table 6 of the present application.

Preparation

A composition comprising (i) a population of cells of a food fungus, (ii) a food matrix comprising a population of cells of a food fungus or (iii) an extract, fermentation product or metabolite of (i) or (ii) as described above may be comprised in a food product. For example, it may be comprised in bread, cereal, biscuits, butter, spreads (e.g. margarine), cheese, yogurts, beverages or pet foods, for example canned or dry cat or dog food. Other suitable food products will be apparent to a person skilled in the art.

The formulation may be mixed with the ingredients of the food product prior to cooking (e.g. baking) and/or added to the food product after cooking. The results set out herein show that formulations may be incorporated into food products without loss of food quality and remain active after being cooked into food products.

Preferably, in one instance the composition is heterologous or exogenous to the food product i.e. the composition is not naturally present in the food product. In one embodiment the composition is one which would not normally comprise fungal cells or spores, for example those used in blue or soft cheeses, such as any of those referred to herein. In one instance, the composition would normally comprise fugal cells or spores, but they are present at an elevated level, for example at a level of at least double, treble, quadruple or higher compared to the normal level.

Thus, a still further aspect of the invention is a food product comprising (i) a population of cells and/or spores of a food fungus, (ii) a food matrix comprising a population of cells of a food fungus or (iii) an extract, fermentation product or metabolite of (i) or (ii) as described above, for example for use in reducing infection, inflammation or oxidation in an individual, wherein the population matrix or extract is not naturally present in the food product. The food product may also be used in reducing lysosmal damage, acidic, SOD or Ig peroxidise damage, damage caused by hydrogen peroxide and other forms of oxidative damage. The food product may be employed to reduce oxidative damage in general and inflammatory oxidative damage in particular. The food may also be used to promote or stimulate regeneration or healing.

A method of making a food product for reducing or delaying or preventing infection, inflammation or oxidation in an individual is also provided, said method comprising: (i) providing a food product ingredient; (ii) mixing (a) a population of cells of a food fungus, (b) a food matrix, or product of its fermentation comprising a population of cells of a food fungus or (c) an extract, fermentation product or metabolite of (a) or (b) as described above, with said ingredient; (iii) formulating said mixture into a food product.

The food product generated may also be employed to reduce or delay inflammatory, lysomal, acidic, SOD, Ig peroxidise or hydrogen peroxide mediated damage. The composition may be used to reduce or eliminate other forms of oxidative damage, as well as in stimulation of regeneration and/or healing. The composition may be used in treating burns or other skin damage.

Food product ingredients include staple foodstuffs, such as flour, meat, eggs, gelatine, milk, salt, preservatives, and water which are used to produce food products. Sugar may be included. Suitable food product ingredients for use in accordance with the present methods are well-known in the art. The compositions of the invention may comprise any such constituents.

A method of making a food product for reducing or delaying or preventing infection, inflammation or oxidation in an individual is also provided, said method comprising: (i) providing a food product, and (ii) incorporating (a) a population of cells of a food fungus, (b) a food matrix comprising a population of cells of a food fungus or (c) an extract, fermentation product or metabolite of (a) or (b) as described above, into said food product. Preferably, (a), (b) and/or (c) are heterologous or exogenous to the food product i.e. (a), (b) and (c) are not naturally present in the food product.

The following is a list of some further numbered embodiments of the invention:

(1) A composition comprising (i) a population of cells of a food fungus, (ii) a food matrix comprising a population of cells of a food fungus or (iii) an extract, fermentation product or metabolite of (i) or (ii) for use in the reduction or inhibition of infection, inflammation or oxidation in an individual.
(2) Use of a composition comprising (i) a population of cells of a food fungus (ii) a food matrix comprising a population of cells of a food fungus or (iii) an extract, fermentation product or metabolite of (i) or (ii) in the manufacture of a preparation for use in the reduction or inhibition of infection, inflammation or oxidation in an individual.
(3) A method of reducing or inhibiting infection, inflammation or oxidation in an individual comprising; administering a composition comprising; (i) a population of cells of a food fungus, (ii) a food matrix comprising a population of cells of a food fungus, or; (iii) a fraction, extract, fermentation product or metabolite of (i) or (ii), to an individual in need thereof.
(4) A composition, method or use according to any one of claims 1 to 3 wherein the composition reduces or inhibits infection, inflammation or oxidation or the risk thereof in the individual.
(5) A composition, method or use according to any one of (1) to (4) wherein the food fungus is selected from a fungus of the *Penicillium* genus; a fungus of the *Rhizopus* genus; a fungus of the *Fusarium* genus; or a fungus of the *Monascus* genus; or a fungus of the *Aspergillus* genus.
(6) A composition, method or use according to any one of (1) to (5) wherein the fungus of the *Penicillium* genus is selected from *Penicillium roqueforti; Penicillium camemberti; Penicillium candidum; Penicillium glaucum*; and *Penicillium nalgiovense*
(7) A composition, method or use according to any one of (1) to (6) wherein the composition is a fortified food; a food additive; a dietary supplement; a nutraceutical product; a pharmaceutical product; a topical dermatological product or a topical cosmetic product.
(8) A composition, method or use according to any one of (1) to (6) wherein the composition is a food product or beverage.
(9) A composition, method or use according to any one of (1) to (8) wherein the food matrix is selected from a dairy product; meat; or beverage; or other biological matrixes.
(10) A composition, method or use according to (9) wherein the food matrix is a cheese.
(11) A composition, method or use according to (10) wherein the cheese is selected from the group consisting of: Roquefort; Camembert; Creamy Blue; Stilton; Cabrales, Cambozola; Fourme d'Ambert; Gorgonzola; Bleu d'Auvergne; Cibosano.
(12) A composition, method or use according to any one of (1) to (11) wherein the extract is produced by admixing the food matrix with a liquid phase and isolating the liquid phase.
(13) A composition, method or use according to (12) wherein the liquid phase is an aqueous or non-aqueous solvent.
(14) A composition, method or use according to (13) wherein the liquid phase is selected from the group consisting of: phosphate buffered saline (PBS); methanol; ethanol; hydrochloric acid; and ethanol and hydrochloric acid.
(15) A composition, method or use according to any one of (12) to (14) wherein the liquid phase is isolated by centrifugation or filtration.
(16) A composition, method or use according to any one of (12) to (14) wherein the liquid phase is sterilized or pasteurized following said isolation.
(17) A composition, method or use according to any one of (1) to (16) wherein the composition reduces or inhibits one or more of allergic processes; endothelial damage; inflammation; oxidative damage; inflammatory oxidative damage; inflammation in the development of organ diseases; and recruitment of pro-inflammatory cytokines in an individual.
(18) A composition, method or use according to any one of (1) to (17) wherein the individual has a condition selected from the group consisting of auto-immune disease; hypertension; atherosclerosis; cardio pathologies; vascular pathologies; cerebral pathologies; obesity; diabetes type 2; cancer, sarcopenia; metabolic dysfunction; gastritis; stomach or duodenum ulcers; arthritis or joint disease; dermatitis; psoriasis; acne; chronic skin ulcerations, age-related or non-age related skin conditions; skin and other tissue burns and wounds; injuries, including sport, trauma, operative and other injuries; cachexia; side-effects of chemotherapies and radiation treatment; and radiation exposure.
(19) A composition, method or use according to any one of (1) to (18) wherein the composition has an assigned grade which is indicative of the activity of the reduction or inhibition of infection, inflammation or oxidation.
(20) A composition, method or use according to (19) wherein the assigned grade or score is displayed on the composition or its packaging.
(21) A method of identifying and/or characterizing a food product comprising (i) providing a food product comprising a population of cells of a food fungus and; (ii) measuring the activity of the food product or an extract thereof in reducing infection, inflammation or oxidation.
(22) A method according to (21) comprising, before step (i), selecting or identifying a food product which comprises a population of cells of a food fungus.
(23) A method according to (21) or (22) comprising assigning a score or grade to the food product which is indicative of said measured activity.
(24) A method according to (23) comprising marking or labeling the food product or its packaging with the assigned score or grade.
(25) A method for producing an extract for use in reducing infection, inflammation or oxidation in an individual, comprising: a) providing a food matrix comprising a population of cells of a food fungus; b) admixing said food matrix in a liquid phase and;

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures and tables described below.

EXAMPLES

Tested Cheeses

For most experiments presented, here the main source of cheese extracts was Roquefort cheese made from ewe's milk. Roquefort is made in the Midi-Pyrenees. In preliminary experiments two brands (FIG. 1, top) were tested. Both demonstrated similar anti-bacterial and anti-oxidative properties. For the results presented below, extracts were obtained from "regular" Roquefort (FIG. 1, top left) and not from the "golden medal" Roquefort (FIG. 1, top right). Roquefort from which extracts were obtained is made from unpasteurised untreated whole ewe's milk utilizing *Penicillium roqueforti*. Ossay-Iraty was used as a control cheese (FIG. 1, bottom). This cheese is from the Basque region of France, a region neighboring the Midi-Pyrenees. Ossay-Iraty cheese is also made from unpasteurised untreated whole ewe's milk, but does not contain food fungus.

Figure 2:
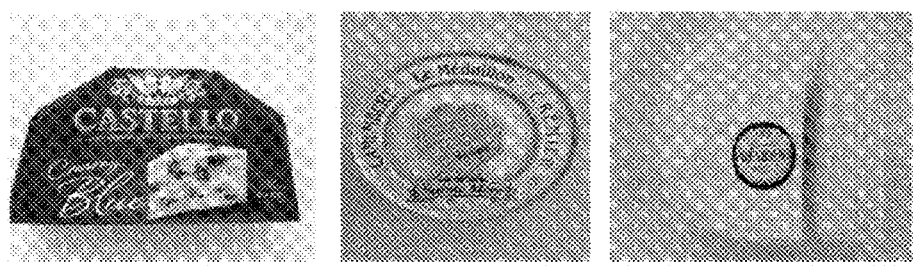
FIG. 2 shows examples of Castello® cheese and two Camembert cheeses.

To assess whether the observed effects are unique to cheeses made from ewe's milk, cow's milk cheeses containing *Penicillium roqueforti* were also tested (e.g. Danish Blue Cheese; Castello, DK) (FIG. 2*a*). To assess whether the observed effects are unique to a particular fungus, Camembert cheeses produced using *Penicillium camemberti* were also tested. Unpasteurised Camembert Le Medaillon Cremier (FIG. 2*b*), and pasteurized, Camembert President (FIG. 2*c*) were tested.

Preparation of Cheese Extracts

Figure 3:
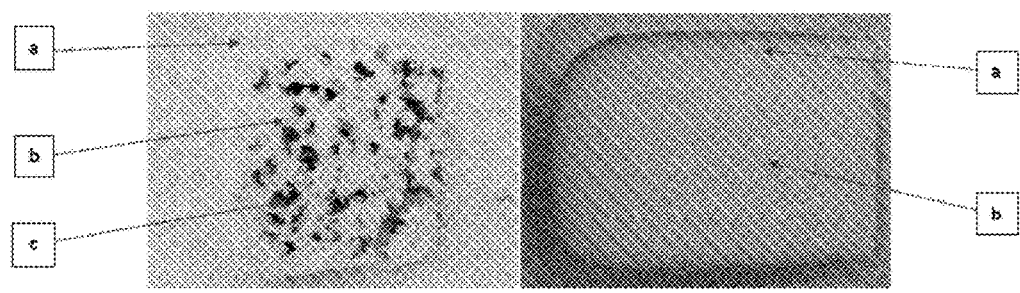
FIG. 3 shows the regions of Roquefort and Ossay-Iraty cheeses from which portions were selected to make extracts. Left—Roquefort: a) approximately 5 mm from the surface and no less than 10-15 mm from the edge of the nearest fungal colony; b) 5 mm from the edge of a fungal colony; and c) from the region of most intensive growth within the fungal colony—the fungal nucleolus. Right—Ossay-Iraty: a) 5-10 mm from the crust; b) from the middle part of the cheese.

Extracts of Roquefort were obtained from three different parts of the cheese: (a) about 5 min from the surface of the cheese and no less than 10-15 mm from the edge of the nearest fungal colony; (b) about 5 mm from a fungal colony; and (c) from the region of most intensive growth within a fungal colony described herein as a fungal nucleolus (FIG. 3).

Extracts of Castello® cheese were obtained from the same regions. Extracts of Camembert were obtained from three different regions of the cheese: (a) the middle part of the cheese; (b) 5-10 mm from the surface; and (c) from the crust.

Extracts of Ossay-Iraty were obtained from two regions of the cheese: (a) 5-10 mm from the crust; and (b) from the middle part of the cheese (FIG. 3).

Preparation of Extracts and Fractions

Food fungus extracts were produced by adding an equal volume of PBS to each cheese portion, for example, 10-15 ml of PBS was added to 10-15 g of each cheese. The samples were then homogenized in a temperature controlled vortex for 10 minutes.

Homogenised suspensions were incubated for 1 hour at 4° C., and then the samples were centrifuged for 15 mins at 3,500 rpm, Eppendorf 5810R. The supernatant was centrifuged for another 15 mins at 16,000 rpm, Eppendorf 5115D. The supernatant was used for further fractionation.

Extracts were fractionated by gel-filtration on a column (1.5×9.0 cm) with Sephadex G-25 Medium in PBS. The column was pre-calibrated to determine the free and the total volume by using Dextran Blue and DNP-L-Ala. For each experiment 3 ml of cheese extract was introduced to the column, then the eluting fractions were collected in the following volume: fraction "1" in 6 ml; fraction "2" in 4 ml; and fraction "3" in 10 ml. Protein concentrations were determined by absorption at 280 nm, Shimadzu UV-1,800. Results of a typical experiment are presented in Table 1.

Electrophoresis

Figure 4:
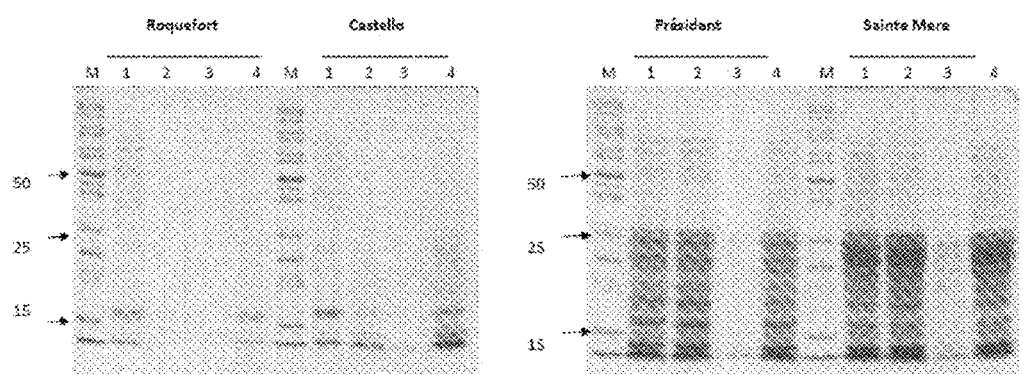
FIG. 4 shows protein electrophoresis in SDS polyacrylamide gel. M—molecular mass (protein standard). 1-3 eluted fractions. 4 initial PBS cheese extracts.

To determine the protein profile of each fraction, protein fractions were subjected to electrophoresis in polyacrylamide gel in SDS using the Laemmli method. All fractions were diluted 10 fold in PBS. Fractions were then diluted further; Fraction "1" of Castello® was diluted 2 fold, fraction "1" of Camembert Medallion and fraction "1" of Camembert President were diluted 5 fold each, fraction "1" of Roquefort was used without dilution. Other fractions were also used without dilutions. Then all samples were diluted by Laemmli buffer containing 2-mercaptoethanol, and heated for 5 mins at 100° C. For analysis 10 µl of each sample was used. For electrophoresis MiniProtean III was used at 200 W. Commercial protein standards had a molecular mass of between 10,000 and 200,000 kD. To verify protein bands the gel CBB G-250 was used. Electrophoresis results are shown in FIG. 4.

Ethanol Fractions

An equal volume of 99% ethanol was added to cheese portions, for example 10-15 ml of 99% ethanol was added to 10-15 g of cheese. The samples were homogenised. Homogenised suspensions were incubated for 1 hour at 4° C., and then samples were centrifuged for 15 mins at 3,500 rpm, Eppendorf 5810R. The supernatant was repeatedly centrifuged for another 15 mins at 16,000 rpm, Eppendorf 5115D. This supernatant was used in further experiments.

Further ethanol:HCL fractions were obtained by homogenizing the cheese portion with 50:50 99% ethanol: 0.01M of hydrochloric. This was to imitate stomach acidity during digestion. Homogenised suspensions were incubated for 1 hour at 4° C., and then samples were centrifuged for 15 mins at 3,500 rpm, Eppendorf 5810R. The supernatant was repeatedly centrifuged for another 15 mins at 16,000 rpm, Eppendorf 5115D. This supernatant was used in further experiments.

Finally, fractions were centrifuged to remove any visible cheese particles and the samples were then sterilised by filtration via 0.22 µm pore membranes.

Anti-Bacterial and Anti Fungal Activities

To test for anti-bacterial and anti-fungal properties, three common bacteria and one fungus were used in experiments:

*Escherichia coli*, strain ATCC 25922,
*Staphylococcus saprophyticus*, ATCC 15305,
*Chlamydia trachomatis*, strain L2/43/Bu,
*Candida albicans*, ATCC 10231.

*Escherichia coli*, *Staphylococcus saprophyticus* and *Candida albicans* were incubated for 24 hours on agar medium in a petri dish in the presence and absence of cheese extracts. *Chlamydia trachomatis* in HeLa cell culture was incubated for 24 hours in the presence and absence of cheese extracts.

Ossay-Iraty cheese extracts (a) and (b), with protein concentrations between 2 µg and 200 µg, did not have any effect on the growth of any of the microorganisms. Roquefort extracts were all active, while the most prominent effects were observed for extracts obtained from region (b). The results are presented in Table 2.

Despite displaying significant anti-bacterial and anti-fungal properties, the cheese extracts did not completely inhibit the tested microorganisms. However, this data shows that cheese extracts may be useful in the treatment and/or prevention of infection.

Activity Against *Chlamydia trachomatis* (In Vitro)

The effect of the cheese extracts was tested using *Chlamydia trachomatis* L2/43/Bu strain grown on the cell line U-937, which is derived from male diffuse histiocytic lymphoma. Cell suspensions were grown in 7 ml of RPMI-1640 with 10% foetal calf serum in cell culture flasks (Corning) under 37° C. in 5% $CO_2$ atmosphere. Cell culture was sub-cultured every 2 days. The cell suspensions contained $6 \times 10^6$ cells per 1 ml. The experiment was conducted in 24-well plates. Immediately after aliquoting the cell suspension into the wells each well was inoculated with *C. trachomatis* L2/43/Bu in 10 MOI. At the same time, different doses of cheese extracts were introduced into each well. Uninfected cell suspensions were used as a control. After inoculation and addition of cheese extracts all plates were centrifuged at 3,000 g (1,800 rpm) for 20 mins at 25° C., and then incubated for 24 h at 37° C. in 5% $CO_2$ atmosphere.

Ossay-Iraty extracts did not inhibit *Chlamydia* growth at any of the tested concentrations, from 2 to 200 µg/ml of the cell culture media. Roquefort extracts showed a significant inhibitory effect on the growth of *Chlamydia* bacteria. The results are presented in the Table 3.

Activity Against *Chlamydia* Infection In Vivo

Twelve female BALB/c mice, with body masses between 24-25 g were divided into three groups. The control group was fed with Ossay-Iraty cheese, group one was fed Roquefort cheese, group two was fed Danish blue cheese (Creamy blue cheese, Castello®).

Initially mice were kept under observation and fed with the cheeses. The mice ate Roquefort or Danish blue cheeses and their body mass was maintained. The mice in the control group consumed Ossay-Iraty without an observable problem. After one week of observation all mice were intranasally inoculated with *Chlamydia muridarum*, strain MoPn, originally named Nigg. Each mouse received 5-10$^4$ of bacteria. The cheese diets were maintained in each group.

On the third day after inoculation all mice in the control group died from pneumonia and septicaemia. On the fourth day two mice died in each of the other two groups. All surviving animals were then sacrificed for post-mortem examination.

Post-mortem revealed that the lungs of the animals from the control group contained massive clusters of lesions heavily infected with *Chlamydia* bacteria. The lungs of mice from groups one and two, fed on Roquefort and Danish blue cheeses, showed significantly reduced levels of *Chlamydia* infection compared to the control group. The only noticeable anomaly found in the dead mice from groups one and two was a significantly enlarged liver, which may explain the fatal outcome. Therefore, Roquefort and Danish blue cheeses contain a which can prevent and/or inhibit the development of acute *Chlamydia* pneumonia.

Anti-Inflammatory Properties

Effect of Cheese Extract on Cytokine Production

*Penicillium roqueforti* and/or molecules produced by *Penicillium roqueforti* grown on a ewe's or cow's milk substrate, are shown above to inhibit *Chlamydia* infection in vitro and in vivo. Extracts of Roquefort from regions (a) and (b) were tested for the ability to suppress or inhibit production of key cytokines during cell culture inoculated with *Chlamydia*.

The cell line, the *Chlamydia* strain and the protocol were as described above.

After incubating the cells for 24 h at 37° C. in 5% $CO_2$ atmosphere, 150 µl of each suspension was transferred into Eppendorf tubes (0.5 ml) and then centrifuged for 5 mins at 3,000 g (1,800 rpm). After that 100 µl of the supernatant were transferred into new tubes and diluted 1,000 fold by PBS. The samples were analysed by Bio-Plex (Bio-Rad) and M50000007A Human 8-Plex Cytokine Panel for the following cytokines IL-1B, IL2, IL-4, IL-6, IL-8, IL-10, BM-CSF (bovine macrophage colony-stimulating factor), IFN-γ, and TNF-α.

The results are presented in the table 4. Both extracts (a) and (b) of Roquefort cheese were able to significantly suppress production of all tested cytokines apart from BM-CSF and INF-γ. It was observed that the effect of extracts obtained from region (b) were significantly more effective than extracts obtained from region (a). This was particularly evident at the lower concentration of 20 µg of protein. At this concentration extracts obtained from region (b) were 3 times more effective at inhibiting TNF-α production than extracts obtained from region (a). For IL-1β the difference was 4 fold.

The inhibition of cytokine production was accompanied by 80-85% inhibition of *Chlamydia* growth for extracts obtained from region (a), while extracts obtained from region (b) completely blocked propagation of *Chlamydia* infection (table 4).

Roquefort and Danish Blue Cheeses Modulate LPS-mediated cell Recruitment to the Peritoneal Cavity The anti-inflammatory properties of Roquefort (RS) and Castello (Cast) cheeses were analysed in mice with LPS induced inflammation.

Mice were fed via gavage needle with 0.2 ml of cheese extract for 2 days (twice daily) before intraperitoneal (i.p.) injection of 0.5 mg/kg LPS *E. coli* (Sigma). Two days later peritoneal washes were obtained from mice fed with cheese extracts and control mice not fed with cheese extracts (LPS or saline only). Counted and recruited cell populations (neutrophils, macrophages, T and B cells) were analyzed by flow cytometry (Flow cytometer—FACS Calibur (BD), software—CellQuest (BD) and FCS express (DeNovo software).

Figure 5:
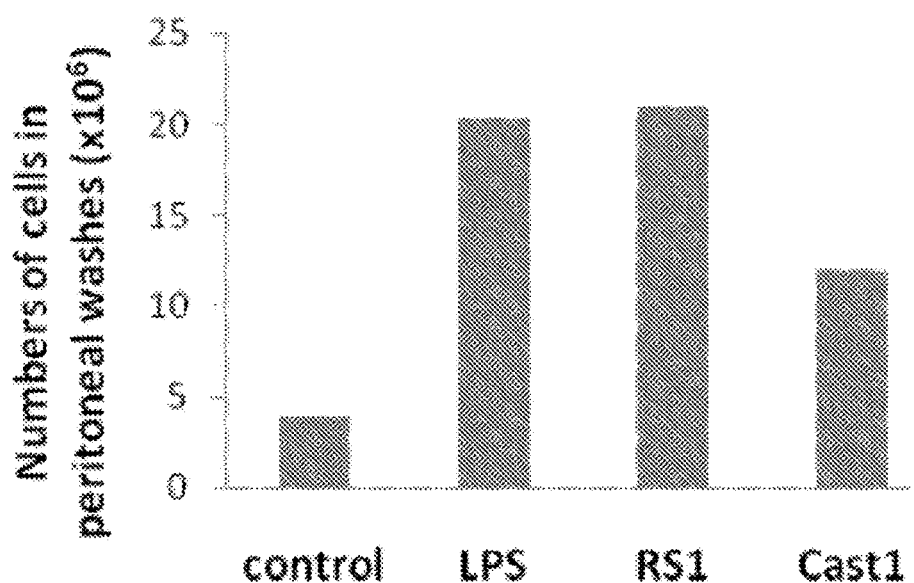
FIG. 5 shows the total numbers of cells recruited to the peritoneal cavity in response to LPS intraperitoneal (i.p.) challenge: control—saline only; LPS—LPS i.p challenge only; RS1 - roquefort fed mice; Cast1—Castello fed mice.

The total number of cells recruited to the peritoneal cavity in response to LPS challenge was increased at day 2 (FIG. 5). Mice fed with extracts obtained from Castello® cheese showed reduced LPS-induced inflammatory cell recruitment. This might also affect the severity of inflammation.

Figure 6:
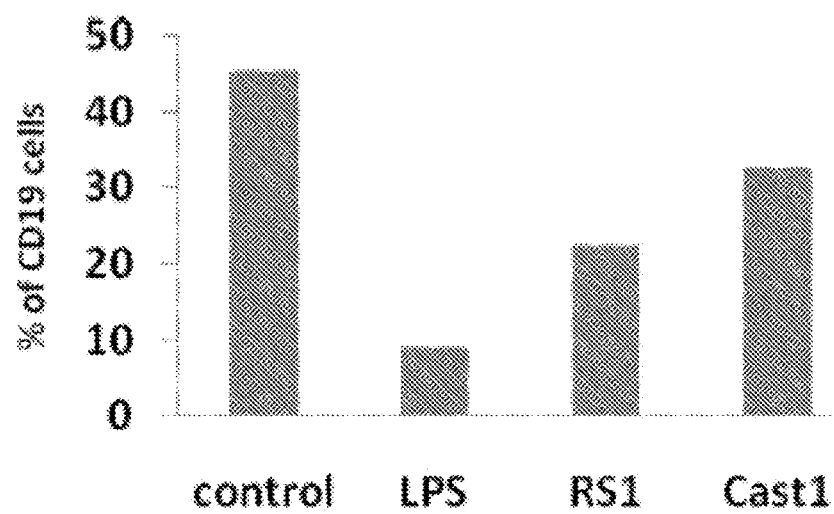
FIG. 6 shows the number of B cells recruited in response to LPS i.p. challenge for each of: control-saline only; LPS—LPS i.p challenge only; RS1 —roquefort fed mice; Cast1 —Castello fed mice.
Figure 7:
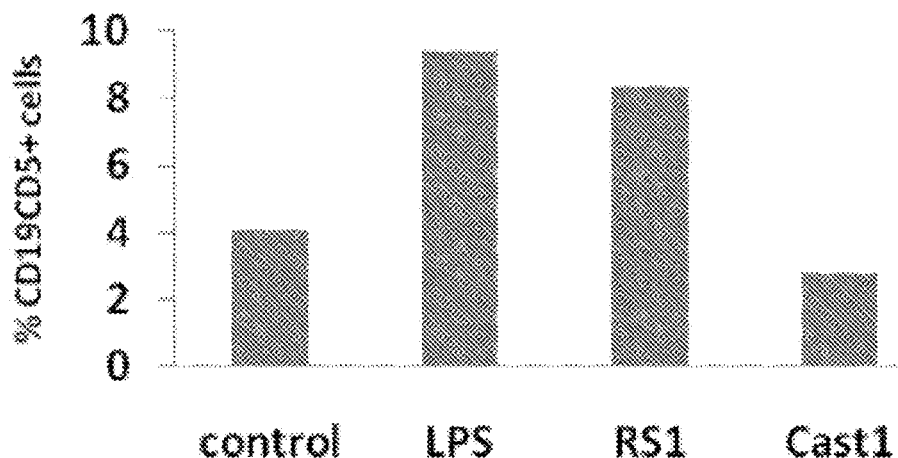
FIG. 7 shows the number of B-1 cells recruited in response to LPS i.p. challenge for each of: control-saline only; LPS—LPS i.p challenge only; RS1—roquefort fed mice; Cast1—Castello fed mice.
Figure 8:
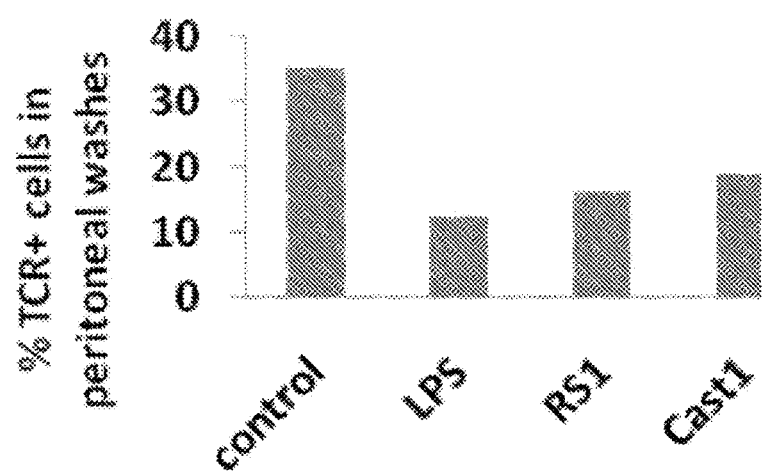
FIG. 8 shows the numbers of T cells recruited in response to LPS i.p. challenge for each of: control-saline only; LPS—LPS i.p challenge only; RS1—roquefort fed mice; Cast1—Castello fed mice.

The number of B cells was reduced in response to LPS at day 2 after treatment (FIG. 6). Treatment with cheese extracts attenuated B cell loss after LPS treatment, which might result in better resistance to inflammation. B-1 cell subpopulations are non-specific B cell populations that participate in innate resistance to various infections and some inflammatory disorders. The number of B-1 cells (CD19+CD5+) increased in LPS and RS+LPS treated groups and were almost normal in the Cast+LPS treated group (FIG. 7). Increased T cell numbers were also observed in mice fed with cheese extracts (FIG. 8)

Figure 9:
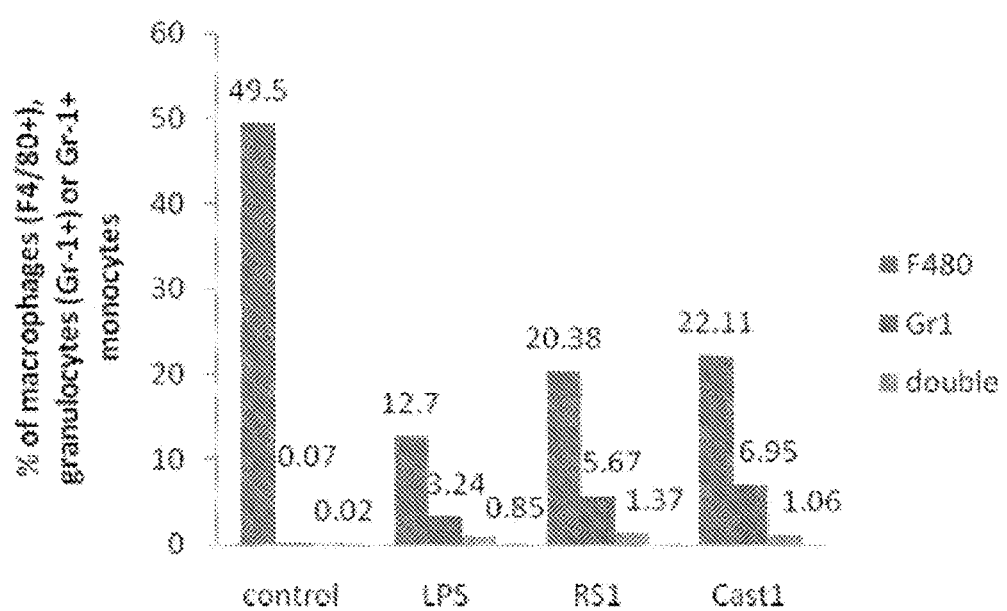
FIG. 9 shows numbers of neutrophils and macrophages recruited in response to LPS i.p. challenge for each of: control-saline only; LPS—LPS i.p challenge only; RS1—roquefort fed mice; Cast1—Castello fed mice.

The number of resident macrophages in the peritoneal cavity was also reduced in LPS treated mice and but was increased in mice fed with cheese extracts (FIG. 9). There were almost no neutrophils in control mice but there was an increase in the number of these cells after LPS treatment. There were slightly higher levels of these cells in mice fed with cheese extracts.

Even short-term (2 days) feeding with cheese extracts demonstrates an apparent capacity to modulate cell recruitment in the response to i.p. LPS challenge with the tendency to restore the loss of B, T and macrophage subpopulations in response to inflammatory challenge. This capacity affects cells involved in both innate and adaptive immunity suggesting long-term regulation of inflammation is possible.

Inhibition of Inflammatory Oxidative Damage

1. The Effect of Food Fungi Products or their Extracts on Inflammatory Oxidative Damage Ex-Vivo Assay A sample of a homogenate of a human tissue recovered from an operation, or human plasma or serum, particularly from an individual with an inflammatory condition, is provided and adjusted with PBS to a concentration of 5 or 6 mg of protein per 1 ml. Then a test sample is introduced such that addition does not dilute the tissue homogenate more than 5%.

The sample is then divided in two parts. To one sample, hydrogen ions, a substrate for superoxide dismutase, in the form of acetic or hydrochloric acid, but not, for example, sulfuric acid, is added in a concentration of 100 fold above the control sample, where only PBS was added in the same volume. Both samples are incubated over night, or at a standardized time of not less than 6 and no more than 24 hours. Then the reaction is stopped by 0.5-1M trichloric acid, and the standard MDA test performed to measure the level of the oxidised tissue.

2. The Effect of Food Fungi Products or their Extracts on SOD-peroxidaseactivity in Vitro Assay The test system contained 0.1-100 ng of $Cu^{2+},Zn^{2+}$-SOD and its substrate 1-1,000 μM of human LDL in 0.01-0.05M acetic, or phosphate or their combination, buffer at pH 4.0-5.4-6.5-7.0.

To boost the reaction, in some cases, a biochemical or electrochemical superoxide generated system may be added. For example, 1 μM-1 mM of cytochrome C and 0.1 ng to 0.1 mg of cytochrome C oxidase, or 0.1 μM-10 mM of xanthine and 0.1 ng-0.1 mg of xanthine oxidase.

The tested samples may be added in concentration of 0.1 ng to 10 mg of protein and incubated for 1 hour, 2-4 hours or overnight at 37° C. Then either diene conjugates, or hydroxyl peroxide, or MDA or other molecules or radical groups, as products of peroxidation were measured.

The concentration of these products of peroxidation is compared with control samples where instead of fungal products PBS or other extracting or diluting solvents were used.

The following experiment demonstrates the effect of cheese extracts on oxidative damage resulting from inflammation, as measured using the above described assays. Scientific rationale of the methodology is described elsewhere [1-3].

The anti-IOD properties of different cheese extracts were investigated. Ossay-Iraty cheese did not have a significant effect on the level of inflammatory oxidative damage (IOD) in the test system. On the other hand extracts from three other cheeses were able to inhibit this process (table 6). The most significant results were observed using extracts derived from region b of the cheese. Results for extracts obtained from Castello cheese demonstrate that extracts homogenized in PBS were effective inhibitors of IOD, higher molecular weight extracts were most effective. Low molecular weight extracts obtained from Camembert President were most effective. Both low and high molecular weight extracts obtained from Camember Le Medallion were effective. Extracts obtained from Roquefort and dissolved in PBS were not as effective as the extracts obtained from Castello, Camembert President and Camembert Le Medallion.

Extracts obtained from Castello and Roquefort homogenized in PBS, and fractions of these extracts, contained significantly less protein than the two Camembert cheeses according electrophoresis data (FIG. 4). Therefore it possible to suggest that the anti-IOD activity is due to polysaccharides which could be metabolites of and/or parts of *Penicillium roqueforti* grown in the specific conditions during the ripening of this cheese.

Ethanol extracts for all four tested chesses were effective inhibitors of IOD. The addition of hydrochloric acid (HCL) to extracts obtained from Roquefort increased the levels of IOD inhibition. Results are presented in table 7.

Clinical Trial

The impact of the consumption of Roquefort cheese on selected patients with Coronary Heart Diseases (CHD) was assessed. The CHD patients also tested positive for either *Chlamydia pneumoniae* IgG antibodies (ELISA, Medac) and/or presented with elevated total cholesterol.

30 patients were recruited, 16 males and 14 females, aged 45-66 years. These patients were randomised into two equal groups. Three patients did not complete the trial and therefore were removed from the study. The control group consumed Ossau-Iraty cheese. The test group consumed Roquefort cheese. It was recommended to patients that both cheeses were consumed twice daily with a light meal in portions of about 25 grams.

Blood was collected at the start of the trial and after 8 weeks on the cheese diet. The analysis of the blood was blinded. The results of this trial are presented in the table 8.

In the group consuming Roquefort cheese, there was a reduction in titres of *Chlamydia* specific antibodies, in addition the number of *Chlamydia* positive patients was reduced. Prior to the trial only 3 patients were *Chlamydia*-negative, after 8 weeks 6 patients were *Chlamydia* negative. None of the patients in the control group became *Chlamydia*-negative.

A similar trend was observed for total cholesterol concentration. Prior to the trial 4 patients out of 14 from Roquefort cohort exhibited elevated cholesterol levels. After the trial in all patients, bar 1, cholesterol was reduced to 200 mg/dL and below. It is also important to note a significant reduction in LDL cholesterol particles.

There was a reduction in a major group of lipids, triglycerides, and a noticeable trend in the reduction of liver enzymes, ALT and AST (lipids were presented in mg/dL and enzymes in U/ml). The latter were not elevated at the beginning of the trial but nevertheless this trend might indicate some positive changes in the liver. These effects were not observed in the control group. Inflammation of the liver may be a response to the presence of *Chlamydia* and the level of the inflammatory oxidative damage was reduced in patients on the Roquefort diet. This trend extended to blood as shown by MDA concentration (μM). There were no changes in this parameter in the control cheese group.

REFERENCES

1. Petyaev I. M., Hunt J. V. (1996), Redox report, v. 2, No. 6, 365-372.
2. Petyaev I. M. et al (1998), Biochem. Soc. Trans., v. 26, S43
3. Petyaev I. M. (1999) In: Superoxide Dismutase: Recent Advances and Clinical Applications, Paris, 40-44.
4. Petyaev I. M., Coussons P. J. (1999) In: Superoxide Dismutase: Recent Advances and Clinical Applications, Paris, 51-54.
5. Bashmakov Y K, et al (2010), Comp Hepatol., January 28; 9:3.
6. Yuriy K Bashmakov, et al (2010) World Journal of Hepatology, February 27; 2(2):74-80.
7. Petyaev I M, et al (2010), Int J Med. Sci. 2010 Jun. 10; 7(4):181-90
8. Ivan M. Petyaev, et al (2011) HYBRIDOMA, Volume 30, Number 2:131-136.
9. Chalyk N E, et a;. (2009), Klin Lab Diagn. 2009 August; (8):7-8.
10. Petyaev I. Advances in Heart Disease-Proceedings of the 12th World Congress on Heart Disease-New Trends in Research and Treatment. Vanvouver Canada, 2005; July 16-19: 277-283.

TABLE 1

Protein concentration of cheese fractions
(results of a typical experiment)

| Cheeses | Extracts and their fractions | Protein Concentrations |
|---|---|---|
| Roquefort | PBS extract | 36 mg/ml |
|  | PBS-1 | 3.1 mg/ml |

TABLE 1-continued

Protein concentration of cheese fractions
(results of a typical experiment)

| Cheeses | Extracts and their fractions | Protein Concentrations |
|---|---|---|
|  | PBS-2 | 3.4 mg/ml |
|  | PBS-3 | 6.1 mg/ml |
| Castello ® | PBS extract | 51.6 mg/ml |
|  | PBS-1 | 14.6 mg/ml |
|  | PBS-2 | 2.8 mg/ml |
|  | PBS-3 | 1.8 mg/ml |
| Camembert Sainte Mere | PBS extract | 66.8 mg/ml |
|  | PBS-1 | 26.6 mg/ml |
|  | PBS-2 | 7.8 mg/ml |
|  | PBS-3 | 1.7 mg/ml |
| Camembert President | PBS extract | 66.8 mg/ml |
|  | PBS-1 | 29.6 mg/ml |
|  | PBS-2 | 6.6 mg/ml |
|  | PBS-3 | 0.9 mg/ml |

TABLE 2

Dose-dependent effect of Roquefort cheese extract (b) on the growth of *E. coli, S. saprophyticus* and *Candida*\*.

| Micro-organisms | Number of microorganisms after addition of Roquefort cheese extract (b) to the culture media (μg protein/ml\*\*) | | | | |
|---|---|---|---|---|---|
|  | 0 | 25 | 50 | 75 | 100 |
| *Escherichia coli* | $10^8$ | $10^8$ | $10^7$ | $10^6$ | $10^6$ |
| *Staphylococcus saprophyticus* | $10^7$ | $10^7$ | $10^7$ | $10^6$ | $10^6$ |
| *Candida albicans* | $10^6$ | $10^6$ | $10^5$ | $10^4$ | $10^4$ |

\*Concentration of the microorganisms on the start of the experiment was $10^6$ KOE/ml.
\*\*Incubation was for 18 hours at 37° C.

TABLE 3

The effects of PBS extracts and fractions on the growth of *Chlamydia trachomatis* in cell culture.

| Cheeses and their fractions | Concentration | Effect on growth of *Chlamydia trachomatis* |
|---|---|---|
| Roquefort |  |  |
| PBS-1 | 62 μg/ml | Inhibition |
|  | 150 μg/ml | Full inhibition |
| PBS-2 | 69 μg/ml | No effect |
| PBS-3 | 305 μg/ml | No effect |
| Castello ® |  |  |
| PBS-1 | 292 μg/ml | Inhibition |
| PBS-2 | 56 μg/ml | No effect |
| PBS-3 | 90 μg/ml | No effect |
| Camembert Sainte Mere |  |  |
| PBS-1 | 532 μg/ml | No effect |
| PBS-2 | 156 μg/ml | No effect |
| PBS-3 | 85 μg/ml | No effect |
| Camembert President |  |  |
| PBS-1 | 1,480 μg/ml | Inhibition |
| PBS-2 | 132 μg/ml | No effect |
| PBS-3 | 45 μg/ml | No effect |

TABLE 4

Effect of extracts from regions (a) and (b) of Roquefort cheese on the production of cytokines* in cell culture 48 hours after inoculation with *Chlamydia trachomatis*

| | Concentration of cytokines in pg/ml | | | | | | | | Effect on |
|---|---|---|---|---|---|---|---|---|---|
| | TNF-α | IL-4 | IL-6 | IL-8 | IL-10 | BM-CSF | IFN-γ | IL-1β | *C. trahomatis*, infection |
| Negative control | \*2.41 | OOR< | 5.47 | 1022.59 | OOR< | OOR< | 57.83 | 4.42 |  |
| Positive control *C. trachomatis* L2 | 1033.51 | 9.54 | 8324.56 | $151 \times 10^6$ | 52.1 | $24 \times 10^6$ | $4.6 \times 10^6$ | 21487 | 60% of cells infected - large clusters of bacteria |
| +Roquefort cheese | | | | | | | | | |
| +fraction "b", 20 μg protein | 219.61 | OOR< | 49.09 | $22 \times 10^6$ | OOR< | $25 \times 10^6$ | $4 \times 10^6$ | \*2.86 | Single isolated infected cells |
| +fraction "b", 40 μg protein | 113.27 | 0.48 | 23.2 | $17 \times 10^6$ | OOR< | $28 \times 10^6$ | $5.2 \times 10^6$ | \*3.54 | Infected cells are not detected |
| +fraction "a" 20 μg protein | 698.21 | 1.5 | 89.21 | $29 \times 10^6$ | 5.13 | $19 \times 10^6$ | $2.7 \times 10^6$ | 11.96 | 20% of cells were infected - small and medium bacterial clusters |
| +fraction "a" 40 μg protein | 310.12 | 0.61 | 36.18 | $27 \times 10^6$ | \*0.67 | $22 \times 10^6$ | $5.1 \times 10^6$ | \*2.86 | 15% of cells infected - small clusters of the bacteria |

\*statistically insignificant
OOR = Out of Range/OOR> = Out of Range Above/OOR< = Out of Range Below

TABLE 5

Antibodies used in the study

| Cell populations | FACS Calibur channel | | | |
|---|---|---|---|---|
| | FL1 | FL2 | FL3 | FL4 |
| B cells | CD19 FITC | CD5 PE | — | CD1d Alexafluor 647 |
| T cells | CD4 FITC | TCR ab-PE | CD8a PerCP | |
| Neutrophils (Gr-1+) and macrophages (F4/80) | Gr-1 FITC | F4/80 | | |

TABLE 6

Inhibition of IOD in ex-vivo* test-system by different cheese fractions**

Level of IOD after 24 h of incubation with different cheese fractions, in µM of MDA***

| Cheeses | Controls | + fraction "a" | + fraction "b" | + fraction "c" |
|---|---|---|---|---|
| Ossay-Iraty (n = 8)**** | 226 ± 19 | 220 ± 27, p > 0.05<br>Δ = 6 | 208 ± 22, p > 0.05<br>Δ = 18 | n/a |
| Roquefort (n = 8)**** | 238 ± 25 | 130 (188) ± 11, p < 0.05<br>Δ = 104 | 74 (172) ± 18, p < 0.01<br>Δ = 164 | 115 (181) ± 14, p < 0.01<br>Δ = 123 |
| Castello (n = 5)**** | 241 ± 21 | 140 ± 17, p < 0.05<br>Δ = 101 | 105 ± 21, p < 0.01<br>Δ = 136 | 130 ± 16, p < 0.01<br>Δ = 111 |
| Camembert (n = 5)**** | 219 ± 23 | 132 ± 18, p < 0.05<br>Δ = 87 | 107 ± 15, p < 0.01<br>Δ = 122 | 114 ± 17, p < 0.01<br>Δ = 105 |

Δ—increment in the level of inflammatory oxidation

*serum from patients with acute inflammatory conditions,

**200 µg of protein per 1 ml of serum,

***MDA—malondialdehyde,

****number of analysed serum samples

TABLE 7

Inhibition of IOD in ex-vivo test-system by different cheese protein fractions and ethanol extracts*

Level of IOD after 24 h of incubation with different cheese fractions, in µM of MDA

| Cheeses | Protein concentrations | PBS extracts and its fractions | | | | Ethanol extracts | | |
|---|---|---|---|---|---|---|---|---|
| | | PBS extract | fraction 1 | fraction 2 | fraction 3 | Added volume | Ethanol extract | Ethanol-HCL extract |
| Roquefort | 10 µg | Δ = 9 | Δ = 0 | Δ = 0 | Δ = 3 | 10 µl | Δ = 42 | Δ = 52 |
| | 30 µg | | Δ = 28 | Δ = 3 | Δ = 23 | 50 µl | Δ = 39 | Δ = 51 |
| | 50 µg | | | | | | | |
| | 150 µg | | | | | | | |
| | 360 µg | | | | | | | |
| Castello | 10 µg | Δ = 49 | Δ = 50 | Δ = 22 | Δ = 7 | 10 µl | Δ = 35 | Δ = 38 |
| | 30 µg | | Δ = 45 | Δ = 27 | Δ = 17 | 50 µl | Δ = 45 | Δ = 44 |
| | 50 µg | | | | | | | |
| | 150 µg | | | | | | | |
| | 516 µg | | | | | | | |
| Camembert President | 10 µg | Δ = 29 | Δ = 13 | Δ = 62 | Δ = 64 | 10 µl | Δ = 44 | Δ = 50 |
| | 30 µg | | Δ = 19 | Δ = 55 | Δ = 65 | 50 µl | Δ = 61 | Δ = 58 |
| | 50 µg | | | | | | | |
| | 150 µg | | | | | | | |
| | 668 µg | | | | | | | |

*abbreviations the same as in the table 6;

Δ—increment in the level of inflammatory oxidation, the average of 3 parallel tastings.

TABLE 8

A. Effect of 8 weeks of administration of Roquefort and Ossau-Iraty on *Chlamydia* infection, blood serum oxidation and lipid profile in CHD patients (Week = 0)

0 week

| | | | Roquefort | | | | | | | | | Ossau-Iraty | | | | | | |
|---|---|---|---|---|---|---|---|---|---|---|---|---|---|---|---|---|---|---|
| ID | MDA | Chl-bs | CH | TG | HDL | LDL | AST | ALT | CRP | ID | MDA | Chl-Abs | CH | TG | HDL | LDL | AST | ALT | CRP |
| 1 | 163 | 1.049 | 205 | 82 | 45 | 149 | 30 | 15 | 5.2 | 1 | 111 | 0.934 | 157 | 61 | 42 | 123 | 20 | 22 | 3.2 |
| 2 | 128 | 0.874 | 200 | 200 | 40 | 163 | 22 | 24 | 7.1 | 2 | 91 | 1.103 | 132 | 81 | 48 | 123 | 24 | 34 | 0.99 |
| 3 | 161 | 0.959 | 208 | 68 | 42 | 129 | 38 | 60 | 4.9 | 3 | 167 | 1.055 | 158 | 77 | 44 | 120 | 22 | 19 | 4.4 |
| 4 | 159 | 0.452 | 207 | 91 | 49 | 127 | 22 | 25 | 3 | 4 | 191 | 1.112 | 160 | 100 | 40 | 125 | 17 | 19 | 2 |
| 5 | 99 | 0.818 | 204 | 105 | 49 | 140 | 26 | 27 | 12.6 | 5 | 111 | 1.217 | 198 | 85 | 52 | 120 | 34 | 36 | 3.5 |
| 6 | 81 | 0.411 | 208 | 130 | 42 | 149 | 28 | 37 | 12.5 | 6 | 112 | 1.004 | 172 | 79 | 49 | 121 | 26 | 29 | 2 |
| 7 | 99 | 0.812 | 204 | 84 | 40 | 119 | 41 | 43 | 15 | 7 | 95 | 0.964 | 233 | 181 | 46 | 152 | 29 | 27 | 13.2 |
| 8 | 65 | 0.413 | 209 | 88 | 47 | 113 | 32 | 34 | 14.5 | 8 | 194 | 0.888 | 209 | 117 | 41 | 143 | 26 | 19 | 10.5 |
| 9 | 61 | 1.229 | 141 | 61 | 49 | 107 | 24 | 36 | 7 | 9 | 143 | 0.867 | 226 | 129 | 39 | 167 | 31 | 28 | 9.7 |
| 10 | 92 | 0.981 | 164 | 86 | 49 | 117 | 26 | 41 | 9.4 | 10 | 87 | 1.003 | 219 | 114 | 45 | 134 | 22 | 21 | 14.6 |
| 11 | 71 | 1.206 | 229 | 76 | 44 | 141 | 44 | 64 | 4.9 | 11 | 92 | 0.912 | 208 | 155 | 40 | 133 | 32 | 35 | 7.8 |
| 12 | 203 | 0.896 | 167 | 73 | 49 | 119 | 26 | 29 | 0.49 | 12 | 64 | 0.856 | 231 | 127 | 43 | 132 | 29 | 31 | 4.5 |
| 13 | 119 | 0.988 | 227 | 113 | 44 | 150 | 31 | 17 | 5.7 | | 121 | 0.993 | 192 | 109 | 44.1 | 133 | 26 | 27 | 6.7 |
| 14 | 29 | 1.206 | 220 | 200 | 39 | 167 | 24 | 29 | 7.5 | | | | | | | | | | |
| | 109 | 0.878 | 200 | 104 | 44.9 | 133 | 31 | 34 | 7.84 | | | | | | | | | | |

B. Effect of 8 weeks of administration of Roquefort and Ossau-Itaty on *Chlamydia* infection, blood serum oxidation and lipid profile in CHD patients (Week = 8)

after 8 weeks

| ID | MDA | Chl-bs | CH | TG | HDL | LDL | AST | ALT | CRP | ID | MDA | Chl-Abs | CH | TG | HDL | LDL | AST | ALT | CRP |
|---|---|---|---|---|---|---|---|---|---|---|---|---|---|---|---|---|---|---|---|
| 1 | 138 | 0.986 | 195 | 80 | 45 | 146 | 30 | 15 | 5.3 | 1 | 104 | 0.845 | 154 | 60 | 43 | 122 | 20 | 21 | 3.1 |
| 2 | 111 | 0.514 | 194 | 187 | 41 | 160 | 22 | 23 | 7 | 2 | 96 | 0.997 | 132 | 80 | 48 | 123 | 24 | 34 | 0.98 |
| 3 | 132 | 0.923 | 200 | 68 | 42 | 128 | 37 | 55 | 4.8 | 3 | 191 | 1.162 | 156 | 77 | 45 | 120 | 22 | 19 | 4.4 |
| 4 | 115 | 0.298 | 197 | 89 | 49 | 123 | 20 | 23 | 3 | 4 | 178 | 1.011 | 161 | 101 | 40 | 121 | 15 | 18 | 2 |
| 5 | 105 | 0.615 | 190 | 95 | 49 | 137 | 27 | 27 | 12.2 | 5 | 99 | 1.022 | 198 | 85 | 51 | 120 | 32 | 36 | 3.7 |
| 6 | 97 | 0.384 | 203 | 126 | 42 | 146 | 29 | 37 | 12.2 | 6 | 109 | 0.961 | 173 | 82 | 49 | 120 | 26 | 27 | 2.6 |
| 7 | 67 | 0.798 | 196 | 84 | 40 | 117 | 40 | 42 | 15.1 | 7 | 98 | 1.000 | 232 | 183 | 46 | 153 | 28 | 30 | 15.2 |
| 8 | 62 | 0.393 | 200 | 85 | 48 | 11 | 30 | 30 | 14.1 | 8 | 185 | 1.012 | 201 | 149 | 42 | 149 | 24 | 27 | 12.4 |
| 9 | 44 | 0.846 | 141 | 61 | 49 | 106 | 23 | 33 | 6.9 | 9 | 164 | 0.994 | 229 | 138 | 40 | 162 | 35 | 29 | 11.2 |
| 10 | 76 | 0.807 | 162 | 88 | 49 | 116 | 26 | 40 | 9.4 | 10 | 101 | 1.095 | 215 | 152 | 44 | 141 | 29 | 25 | 13.5 |
| 11 | 35 | 0.901 | 192 | 70 | 45 | 137 | 42 | 60 | 4.5 | 11 | 83 | 0.832 | 209 | 161 | 39 | 141 | 34 | 36 | 8.2 |
| 12 | 107 | 0.855 | 167 | 71 | 49 | 119 | 24 | 27 | 0.5 | 12 | 97 | 0.971 | 234 | 145 | 40 | 139 | 30 | 29 | 5.1 |
| 13 | 66 | 0.968 | 199 | 82 | 45 | 145 | 30 | 15 | 5.2 | | 125 | 0.992 | 191 | 118 | 43.9 | 134 | 27 | 28 | 6.9 |
| 14 | 99 | 0.875 | 200 | 200 | 40 | 163 | 22 | 24 | 7.1 | | | | | | | | | | |
| | 89.6 | 0.726 | 188 | 99 | 45.2 | 125 | 29 | 32 | 7.66 | | | | | | | | | | |

The invention claimed is:

1. A method for the treatment of infection or the prevention or treatment of inflammation, inflammatory damage, oxidative damage, a stomach condition, intestinal condition or liver inflammatory condition or complication thereof, or for promoting or stimulating healing of tissue, the method comprising administering to an individual in need thereof a composition comprising:
   (i) a fungal fermented cheese comprising a population of cells and/or spores of a food fungus; or
   (ii) an extract, fermentation product or metabolite obtained from said fungal fermented cheese of (i); or
   (iii) a food, beverage or supplement comprising said fungal fermented cheese of (i) or the extract, fermentation product or metabolite of (ii),
   wherein the fungal cells and/or spores are from, or the fungal fermented cheese is made using, *Penicillium roqueforti* or *Penicillium camemberti*.

2. The method of claim 1, where:
   (a) the infection is a *Chlamydia*, or *Helicobacter pylori* infection;
   (b) the inflammatory damage is lysosomal damage, acidic damage, SOD damage, immunoglobulin mediated damage, peroxidase mediated damage, or hydrogen peroxide mediated damage;
   (c) the method promotes or stimulates healing of wounded, burned, ulcerated, or other forms of damaged or aged tissue; and/or
   (d) the composition is a fortified food or beverage, a food additive, a dietary supplement, a nutraceutical product, a pharmaceutical product, a topical dermatological product or a topical cosmetic product.

3. The method of claim 1, wherein the fungal cells and/or spores are from, or the fungal fermented cheese is made using, *Penicillium roqueforti*.

4. The method of claim 1, wherein:
   (a) the method stimulates, or prevents the impairment of, healing of tissue, wherein the composition stimulates, activates or facilitates the healing of wounded, burned, ulcerated, or other forms of damaged or aged tissue;
   (b) the individual has a condition selected from autoimmune disease, hypertension, atherosclerosis, a cardio pathology, a vascular pathology, a cerebral pathology, a metabolic syndrome, obesity, type 2 diabetes, sarcopenia, cachexia, gastritis, a stomach or duodenum ulcer, cancer, metastatic cancer, arthritis or joint disease, dermatitis, psoriasis, acne, chronic skin, mouth or other organ tissue ulceration, an age-related or non-age related skin impairment, skin or other organ or tissue burn or wounds, injury, side-effects of chemotherapy, radiation treatment, or radiation exposure.

5. The method of claim 1 which reduces or inhibits one or more of allergic processes, endothelial damage, inflammation; oxidative damage, inflammatory damage, oxidative damage, lysosomal damage, acidic damage, SOD—or IgG or other immunoglobulin mediated damage, peroxidase damage, hydrogen peroxide induced oxidative damage, inflammation in the development of organ diseases, or recruitment of pro-inflammatory cytokines in the individual.

6. The method of claim 1, where:
   (a) the composition is, or comprises, a blue or white fungal fermented cheese, a foodstuff or a beverage, comprising said cheese or an extract of said cheese;
   (b) the composition is, comprises, or is an extract from a cheese selected from, Roquefort, Camembert, Creamy Blue, Stilton, Cabrales, Cambozola, Fourme d'Ambert, Gorgonzola, Bleu d'Auvergne, Cibosano; or
   (c) the composition is, comprises, or is an extract from Roquefort cheese.

7. The method of claim 1 where the extract is produced by admixing the food matrix with a liquid phase and isolating the liquid phase.

8. The method of claim 1, where:
   (a) the liquid phase is an aqueous or non-aqueous solvent;
   (b) the liquid phase is selected from phosphate buffered saline (PBS), methanol, ethanol, hydrochloric acid, and ethanol with hydrochloric acid;
   (c) the liquid phase is isolated by centrifugation or filtration; and/or
   (d) the liquid phase is sterilized or pasteurized following isolation.

9. The method of claim 1 which controls, reduces or inhibits postprandial and other forms of inflammatory and oxidative stress, postprandial and other forms of cholesterol- and triglyceride-aemias, postprandial formation of large and extra-large chylomicrons 200-600 nm in diameter and above, postprandial and other forms of liver and pancreas steatosis, postprandial and other forms of transient and continues inflammation and/or damage of these organs in the individual.

10. A method for treatment of infection, the method comprising administering to an individual in need thereof a composition comprising a fungal fermented cheese selected from the group consisting of Roquefort, Camembert, Creamy Blue, Stilton, Cabrales, Cambozola, Fourme d'Ambert, Gorgonzola, Bleu d'Auvergne, and Cibosano.

11. The method of claim 10, wherein the method is for treatment of a bacterial infection.

12. The method of claim 10, wherein the method is for treatment of a *Chlamydia* infection.

13. The method of claim 10, wherein the individual has coronary heart disease.

14. A method for treatment of *Chlamydia* infection, the method comprising administering to an individual in need thereof Roquefort cheese.

15. The method of claim 14, wherein the individual has coronary heart disease.

16. The method of claim 4, wherein the cancer is stomach cancer or duodenal cancer.

17. The method of claim 4, wherein the injury is a sport injury, trauma injury, or operation injury.

18. The method of claim 1, wherein the fungal cells and/or spores are from, or the fungal fermented cheese is made using, *Penicillium camemberti*.

* * * * *